US010580137B2

(12) United States Patent
Amit et al.

(10) Patent No.: US 10,580,137 B2
(45) Date of Patent: Mar. 3, 2020

(54) SYSTEMS AND METHODS FOR DETECTING AN INDICATION OF MALIGNANCY IN A SEQUENCE OF ANATOMICAL IMAGES

(71) Applicant: International Business Machines Corporation, Armonk, NY (US)

(72) Inventors: Guy Amit, Ganei Tikva (IL); Omer Hadad, Ramat Gan (IL)

(73) Assignee: International Business Machines Corporation, Armonk, NY (US)

( * ) Notice: Subject to any disclaimer, the term of this patent is extended or adjusted under 35 U.S.C. 154(b) by 207 days.

(21) Appl. No.: 15/883,112

(22) Filed: Jan. 30, 2018

(65) Prior Publication Data

US 2019/0236782 A1    Aug. 1, 2019

(51) Int. Cl.
*A61B 6/00* (2006.01)
*G06K 9/00* (2006.01)
(Continued)

(52) U.S. Cl.
CPC ............ *G06T 7/0016* (2013.01); *A61B 5/055* (2013.01); *A61B 10/0041* (2013.01); *G06N 3/08* (2013.01);
(Continued)

(58) Field of Classification Search
USPC ........ 382/100, 103, 106–107, 128–133, 156, 382/162, 168, 173, 181, 199, 214, 254,
(Continued)

(56) References Cited

U.S. PATENT DOCUMENTS 8,345,940 B2   1/2013 Mattiuzzi et al.
9,721,338 B2   8/2017 Madabhushi et al.
(Continued)

FOREIGN PATENT DOCUMENTS

WO   2017106469   6/2017
WO   2017165801   9/2017

OTHER PUBLICATIONS

Benou et al., "Ensemble of expert deep neural networks for spatio-temporal denoising of contrast-enhanced MRI sequences", Medical Image Analysis, Dec. 2017, pp. 145-159, vol. 42.
(Continued)

*Primary Examiner* — Seyed H Azarian
(74) *Attorney, Agent, or Firm* — G. E. Ehrlich

(57) ABSTRACT

A method for detecting an indication of likelihood of malignancy, comprising: receiving a sequence of anatomical images of a breast of a target individual acquired over a time interval during which contrast is administered, analyzing the sequence of anatomical images to identify: a baseline pre-contrast image denoting lack of contrast, a peak contrast image denoting a peak contrast enhancement, an initial uptake image denoting initial contrast enhancement, and a delayed response image denoting final contrast enhancement, creating a multi-channel image representation comprising: intensity channel including the peak contrast enhanced image, contrast-update channel including the computed difference between the peak contrast enhanced image and the pre-contrast image, and contrast-washout channel including the computed difference between the initial uptake image and the delayed response image, and computing by a trained deep convolutional neural network, a classification category indicative of likelihood of malignancy for the sequence according to the multi-channel image representation.

19 Claims, 12 Drawing Sheets

(51) Int. Cl.
*G06T 7/00* (2017.01)
*G06N 3/08* (2006.01)
*G16H 30/20* (2018.01)
*A61B 10/00* (2006.01)
*A61B 5/055* (2006.01)
*G06F 17/18* (2006.01)

(52) U.S. Cl.
CPC ............. *G16H 30/20* (2018.01); *G06F 17/18* (2013.01); *G06T 2207/10096* (2013.01); *G06T 2207/20016* (2013.01); *G06T 2207/20076* (2013.01); *G06T 2207/20084* (2013.01); *G06T 2207/30068* (2013.01)

(58) Field of Classification Search
USPC ....... 382/274, 276, 285–291, 294, 305, 318; 1/1; 378/4, 21, 28
See application file for complete search history.

(56) References Cited

U.S. PATENT DOCUMENTS

| | | | |
|---|---|---|---|
| 9,972,089 B2* | 5/2018 | Karczmar | G06T 7/0016 |
| 10,438,354 B2* | 10/2019 | Hsieh | G16H 40/40 |
| 2010/0121178 A1 | 5/2010 | Krishnan et al. | |
| 2010/0142786 A1* | 6/2010 | Degani | A61B 5/055 382/131 |
| 2019/0183429 A1* | 6/2019 | Sung | A61B 5/7267 |
| 2019/0220975 A1* | 7/2019 | Hsieh | G06N 3/04 |

OTHER PUBLICATIONS

Levman et al., "Classification of Dynamic Contrast-Enhanced Magnetic Resonance Breast Lesions by Support Vector Machines", IEEE Transactions on Medical Imaging, May 2008, pp. 688-696, vol. 27, Issue 5.

Szabo et al., "Neural Network Approach to the Segmentation and Classification of Dynamic Magnetic Resonance Images of the Breast: Comparison With Empiric and Quantitative Kinetic Parameters", Academic Radiology, Dec. 2004, pp. 1344-1354, vol. 11, Issue 12.

* cited by examiner

| Classifier | Channels | Images | Accuracy | Sens. | Spec. | AUROC |
|---|---|---|---|---|---|---|
| CNN | 3 | 4863 | 0.83 | 0.84 | 0.82 | 0.91 |
| VGG+SVM | 3 | 4863 | 0.71 | 0.80 | 0.61 | 0.81 |
| CNN | 1 | 4863 | 0.78 | 0.82 | 0.74 | 0.85 |
| VGG+SVM | 1 | 4863 | 0.73 | 0.77 | 0.68 | 0.81 |

FIG. 8

| Classifier | Reduction (%) | Patients | Accuracy | Sens. | Spec. | AUROC |
|---|---|---|---|---|---|---|
| CNN | 25 | 93 | 0.80 | 0.84 | 0.75 | 0.89 |
| VGG+SVM | 25 | 93 | 0.60 | 0.81 | 0.53 | 0.72 |
| CNN | 50 | 62 | 0.80 | 0.84 | 0.74 | 0.87 |
| VGG+SVM | 50 | 62 | 0.50 | 0.82 | 0.46 | 0.69 |
| CNN | 75 | 31 | 0.74 | 0.81 | 0.64 | 0.83 |
| VGG+SVM | 75 | 31 | 0.42 | 0.75 | 0.40 | 0.56 |

| Channels | Accuracy | AUC |
|---|---|---|
| 1 | 0.79 ± 0.05 | 0.88 ± 0.05 |
| 3 | 0.84 ± 0.03 | 0.92 ± 0.03 |
| 5 | 0.86 ± 0.02 | 0.94 ± 0.01 |

1104

| | Patients/studies | Slices/lesions | Sensitivity | False-positives |
|---|---|---|---|---|
| Saliency-based detection | 43/50 | 5420/625 | 0.96 | 9.7/slice |
| Slice-based CNN detection[a] | 43/50 | 5420/625 | 0.85 | 0.7/slice |
| Study-based CNN detection[a] | 43/50 | 5420/625 | 0.98 | 7/study |

FIG. 11

SYSTEMS AND METHODS FOR DETECTING AN INDICATION OF MALIGNANCY IN A SEQUENCE OF ANATOMICAL IMAGES

BACKGROUND

The present invention, in some embodiments thereof, relates to automated analysis of anatomical images of the breast(s) and, more specifically, but not exclusively, to systems and methods for computing likelihood of malignancy according to a sequence of anatomical images of the breast(s).

Magnetic Resonance Imaging (MRI) of the breast is widely-used as a screening examination for women at high risk of breast cancer. A typical breast MRI study consists of 1000 to 1500 images, which are traditionally manually interpreted by a radiologist.

SUMMARY

According to a first aspect, a method for detecting an indication of likelihood of malignancy for a sequence of anatomical images, comprises: receiving a sequence of anatomical images of at least one portion of at least one breast of a target individual, wherein the sequence of anatomical images is acquired over a time interval during which contrast is administered to the target individual, analyzing the sequence of anatomical images to identify the following images: (i) a baseline pre-contrast image denoting lack of contrast within the sequence of anatomical images, (ii) a peak contrast image denoting a peak contrast enhancement within the sequence of anatomical images, (iii) an initial uptake image denoting initial contrast enhancement within the sequence of anatomical images, (iv) a delayed response image denoting final contrast enhancement within the sequence of anatomical images, creating a multi-channel image representation of the sequence of anatomical images comprising the following image channels: (A) intensity channel including the peak contrast enhanced image, (B) contrast-update channel including the computed difference between the peak contrast enhanced image and the pre-contrast image, (C) contrast-washout channel including the computed difference between the initial uptake image and the delayed response image, and computing by a trained deep convolutional neural network (CNN), a classification category indicative of likelihood of malignancy for the sequence of anatomical images according to the multi-channel image representation.

According to a second aspect, a method for training a deep convolutional neural network (CNN) for detecting an indication of likelihood of malignancy for a sequence of anatomical images, comprises: for each of a plurality of sample individuals: receiving a respective sequence of anatomical images of at least one portion of at least one breast of a target individual, wherein the sequence of anatomical images are acquired over a time interval during which contrast is administered to the target individual, wherein a sub-set of images of the sequence of anatomical images include a manual delineation of boundaries of a lesion, receiving an indication of the lesion as benign or malignant, analyzing, the sequence of anatomical images to identify the following images: (i) a pre-contrast image denoting lack of contrast within the sequence of anatomical images, (ii) a peak contrast image denoting a peak contrast enhancement within the sequence of anatomical images, (iii) an initial uptake image denoting initial contrast enhancement within the sequence of anatomical images, (iv) a delayed response image denoting final contrast enhancement within the sequence of anatomical images, creating a multi-channel image representation of the sequence of anatomical images comprising the following image channels: (A) intensity channel including the peak contrast enhanced image, (B) contrast-uptake channel including the computed difference between the peak contrast enhanced image and the pre-contrast image, (C) contrast-washout channel including the computed difference between the initial uptake image and the delayed response image, and training a deep CNN to compute a likelihood of malignancy for a sequence of anatomical images of a target individual according to the multi-channel image representation of the plurality of sample individuals.

According to a third aspect, a system for detecting an indication of likelihood of malignancy for a sequence of anatomical images, comprises: a non-transitory memory having stored thereon a code for execution by at least one hardware processor of a computing device, the code comprising: code for receiving a sequence of anatomical images of at least one portion of at least one breast of a target individual, wherein the sequence of anatomical images are acquired over a time interval during which contrast is administered to the target individual, code for analyzing the sequence of anatomical images to identify the following images: (i) a baseline pre-contrast image denoting lack of contrast within the sequence of anatomical images, (ii) a peak contrast image denoting a peak contrast enhancement of the sequence within anatomical images, (iii) an initial uptake image denoting initial contrast enhancement within the sequence of anatomical images, (iv) a delayed response image denoting the final contrast enhancement within the sequence of anatomical images, code for creating a multi-channel image representation of the sequence of anatomical images comprising the following image channels: (A) intensity channel including the peak contrast enhanced image, (B) contrast-update channel including the computed difference between the peak contrast enhanced image and the pre-contrast image, (C) contrast-washout channel including the computed difference between the initial uptake image and the delayed response image, and code for computing by a trained deep convolutional neural network (CNN), a classification category indicative of likelihood of malignancy for the sequence of anatomical images according to the multi-channel image representation.

The systems, apparatus, methods and/or code instructions (stored in a storage device executed by hardware processor(s)) provided herein provide a technical solution to the technical problem of automatically identifying lesions (which may be malignant) in a sequence of images slices of one or both breasts acquired by a 3D anatomical imaging modality (e.g., MRI). The sequence of images are captured over a period of time during which contrast is administered to the target individual. The total number of images for analysis is quite large, and difficult and/or time consuming for a human radiologist to manually analyze correctly. Automatic classification of lesions in the sequence of images captured over time is a challenging technical problem due to several reasons, for example, small available datasets. In particular, there is a lack of publicly available labeled and/or annotated image sets of one or both breasts that include lesions. Standard automated machine learning methods that rely on large data sets cannot be used due to the lack of available training datasets and due to the fact that such machine learning methods are generally designed for classification of natural images and not of medical images which are different.

The systems, apparatus, methods and/or code instructions (stored in a storage device executed by hardware processor(s)) provided herein provide a technical solution to the technical problem of providing accurate classification results when large training dataset are unavailable, and small training datasets are available. The systems, apparatus, methods and/or code instructions (stored in a storage device executed by hardware processor(s)) provided herein may be trained to discriminate between benign and malignant lesions using a small training dataset, for example, on the order of a few hundred images (e.g., less than about 500, 1000, 1500, or 2000 images) from a few dozen patients (e.g., less than about 50, 100, 150, 200, or 250 patients).

The systems, apparatus, methods and/or code instructions (stored in a storage device executed by hardware processor(s)) described herein improve performance of a computing device that performs the automatic detection of likelihood of malignancy in the image sequence captured over time. The improvement in performance may be based on an increase in accuracy of detecting the likelihood of malignancy using existing computing resources (e.g., processor(s), and/or data storage), and/or improving the efficiency of detecting the likelihood of malignancy by a reduction in processing time, a reduction in processor utilization, and/or a reduction in data storage requirements. The systems and/or apparatus and/or methods and/or code instructions described herein may train a neural network to perform the classification of a multi-channel image computed from the sequence of images acquired over the time interval using a relatively small sized training set. The neural network is trained relatively quickly due to the small size of the training set and/or due to the multi-channel image data structure. The small sized training set and/or the multi-channel image requires smaller storage capacity in comparison to larger training sets and/or analysis of a large number of individual images. In another example, the trained neural network that classifies the multi-channel image computed from the sequence of images performs the classification within a relatively short processing time, using relatively fewer processing resources, and/or using relatively smaller data storage requirements. The improvement in performance may include training the neural network and/or applying the neural network to the multi-channel image using less memory, and/or using fewer computational resources (e.g., processor(s) utilization), and/or faster computation time, without sacrificing the accuracy (and in many cases improving the accuracy) of the computation of the likelihood of malignancy for.

In a further implementation form of the first, second, and third aspects, the sequence of anatomical images is extracted as two dimensional slices from three dimensional image data acquired by an MRI machine executed a T1 weighted protocol of a dynamic contrast enhanced (DCE) study.

In a further implementation form of the first, second, and third aspects, the methods further comprise and/or the system further comprises code for computing a patch distinctiveness saliency map by computing a statistical distance between each patch of a plurality of patches of at least one image of the sequence of anatomical images and an average patch along principal components of the plurality of patches, wherein the multi-channel image representation further includes a patch distinctiveness saliency channel that includes the patch distinctiveness saliency map.

In a further implementation form of the first, second, and third aspects, each one of a plurality of patch distinctiveness saliency maps is computed for a respective image of the sequence of anatomical images, and wherein the method further comprises creating a single patch distinctiveness saliency heat map by combining the plurality of patch distinctiveness saliency maps, wherein the patch distinctiveness saliency channel stores the single patch distinctiveness saliency heat map.

In a further implementation form of the first, second, and third aspects, the methods further comprise and/or the system further comprises code for analyzing the patch distinctiveness saliency map to identify candidate regions that include a relatively higher density of salient values compared to non-candidate regions.

In a further implementation form of the first, second, and third aspects, the analyzing is performed by computing a score image according to a score assigned to each pixel according to salient values above a threshold within a region around the pixel, and applying non-maximal suppression to the score image to obtain a binary detection mask that includes the candidate regions indicative of the locations of local maxima.

In a further implementation form of the first, second, and third aspects, the methods further comprise and/or the system further comprises code for cropping the candidate regions from the at least one image, and resizing each cropped candidate region according to the input of the deep CNN, wherein the deep CNN computes a classification category indicative of likelihood of malignancy for each of the candidate regions.

In a further implementation form of the first, second, and third aspects, the deep CNN outputs a binary detection map that includes the candidate regions computed with the classification category indicative of likelihood of malignancy for each of the candidate regions.

In a further implementation form of the first, second, and third aspects, the methods further comprise and/or the system further comprises code for summing the values of the binary detection maps generated for each image of the sequence of anatomical images along a longitudinal axis, to generate a projected heatmap indicative of spatial concentration of candidate regions.

In a further implementation form of the first, second, and third aspects, the methods further comprise and/or the system further comprises code for computing a cross-saliency map that includes for each patch of a plurality of patches of one breast, the corresponding nearest neighbor patch in a contralateral breast, wherein the cross-saliency map stores cross-saliency values indicative of the distinctiveness of each patch of the plurality of patches, the cross-saliency map is computed according to a statistical distance between each patch of a plurality of patches of one breast of at least one image of the sequence of anatomical images and corresponding patches of the contralateral breast of the at least one image, wherein the multi-channel image representation further includes a cross-saliency channel that includes the cross-saliency map.

In a further implementation form of the first, second, and third aspects, each one of a plurality of cross-saliency maps is computed for a respective image of the sequence of anatomical images, wherein the method further comprises creating a single cross-saliency heat map by combining the plurality of cross-saliency maps, wherein the cross-saliency channel stores the single cross-saliency heat map.

In a further implementation form of the first, second, and third aspects, the cross-saliency map is computed by computing a contralateral patch flow according to a flow field between patches of left and right breasts for identifying for each patch of one breast the corresponding nearest neighbor patch in the contralateral breast, wherein a cross-saliency value of the cross-saliency map of each patch is estimated according to an error of the nearest neighbor patch.

In a further implementation form of the first, second, and third aspects, the smooth motion field is assumed for computation of a dense flow field for each pixel by considering a k×k patch around the respective pixel.

In a further implementation form of the first, second, and third aspects, initially, for each pixel location, a random displacement vector is assigned, the random displacement vector marks a location of a corresponding patch in the contralateral breast, wherein a quality of the displacement vector is measured according to a computed distance between a certain patch of one breast and the corresponding patch of the contralateral breast, and further comprising attempting an improvement in displacement of a certain patch of the one breast according to displacement vectors of neighboring patches of the contralateral breast, and iterating between the assignment of the random displacement vector and improvement in displacement while storing the location of the best corresponding patch of the contralateral breast, according to the statistical distance.

In a further implementation form of the first, second, and third aspects, the trained deep neural network includes nine convolutional layers in three consecutive blocks, the first block of the three consecutive blocks includes two 5×5×32 filters with ReLU layers followed by a max pooling layer, the second block of the three consecutive blocks includes four 5×5×32 filters with ReLU layers flowed by an average pooling layer, and the third block of the three consecutive blocks includes three convolutional layers of size 5×5×64, 6×6×64, and 3×3×64 each of the three convolutional layers followed by a ReLU, wherein the trained deep CNN is terminated by a fully connected layer with 128 neurons and a softmax loss layer.

In a further implementation form of the first, second, and third aspects, the methods further comprise and/or the system further comprises code for, each of a plurality of sample individuals, extracting a normal tissue region from a contralateral breast of a certain image of the sequence of anatomical images, wherein the normal tissue region is associated with a label indicative of normal tissue.

In a further implementation form of the first, second, and third aspects, the deep neural network is trained according to stochastic gradient descent, with a batch size of 100 examples, momentum of 0.9, and weight delay of 0.0001, wherein a number of parameters of the deep CNN is less than about 140,000, wherein a number of sample individuals is less than about 200, a number of annotated lesions is less than about 200, a number of labels image less than about 2000.

In a further implementation form of the first, second, and third aspects, the methods further comprise and/or the system further comprises code for computing a patch distinctiveness saliency map by computing a statistical distance between each patch of a plurality of patches of at least one image of the sequence of anatomical images and an average patch along principal components of the plurality of patches, computing a cross-saliency map by computing a statistical distance between each patch of a plurality of patches of one breast of at least one image of the sequence of anatomical images and corresponding patches of the contralateral breast of the at least one image, wherein the multi-channel image representation further includes a patch distinctiveness saliency channel that includes the patch distinctiveness saliency map and a cross-saliency channel that includes the cross-saliency map.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 8 is a table presenting results of the experiment described herein;

FIG. 10 includes a table presenting results of the experiment described herein when a reduced set of patient data was used;

FIG. 11 include tables presenting results of the experiment described herein.

DETAILED DESCRIPTION

Figure 1:
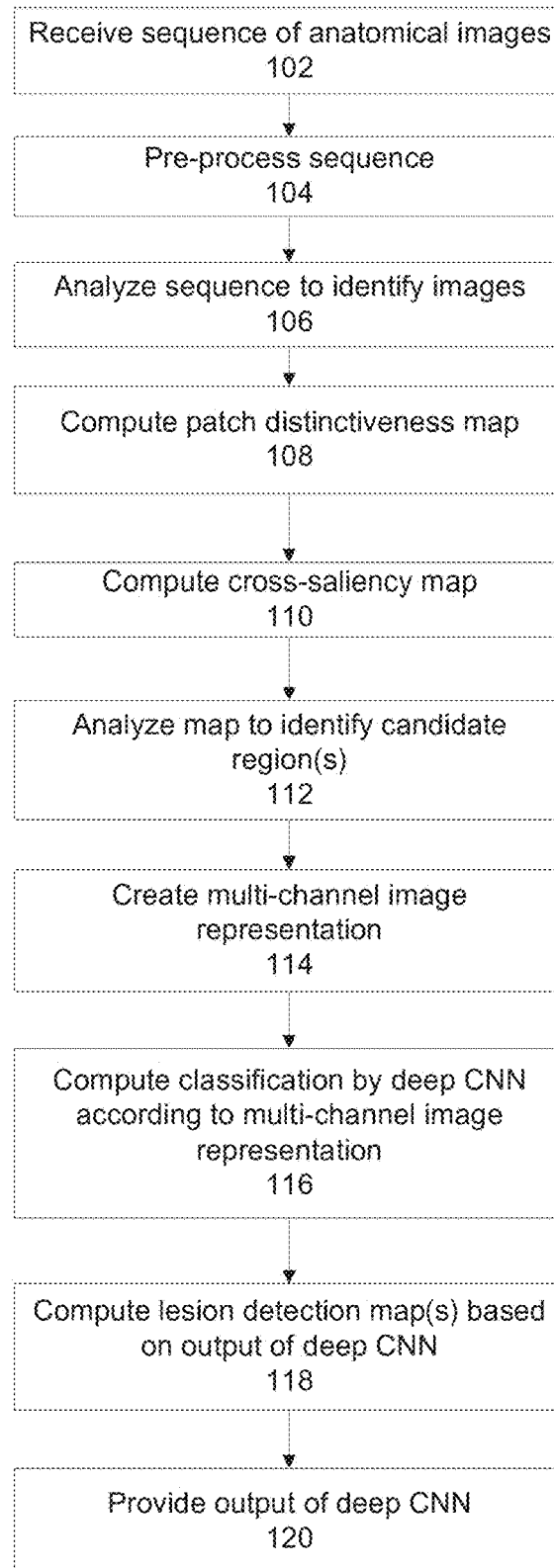
FIG. 1 is a flowchart of a method for computing an indication of likelihood of malignancy in one or both breasts of a target individual by a trained convolutional deep neural network according to a computed multi-channel image, in accordance with some embodiments of the present invention.

The present invention, in some embodiments thereof, relates to automated analysis of anatomical images of the breast(s) and, more specifically, but not exclusively, to systems and methods for computing likelihood of malignancy according to a sequence of anatomical images of the breast(s).

An aspect of some embodiments of the present invention relates to systems, an apparatus, methods, and/or code instructions (stored in a data storage device and executable by hardware processor(s)) for detecting an indication of likelihood of malignancy based on a sequence of anatomical images. The sequence of anatomical images include at least a portion of at least one breast of a target individual. The sequence of anatomical images are acquired over a time interval in which contrast is administered to the target individual. The sequence of anatomical images is analyzed to identify the following images:

Baseline pre-contrast image (also referred to herein as i-base) denoting lack of contrast within the sequence of anatomical images.

Peak contrast image (also referred to herein as i-peak) denoting a peak contrast enhancement within the sequence of anatomical images.

Initial uptake image (also referred to herein as i-early) denoting initial contrast enhancement within the sequence of anatomical images, for example about 2-3 minutes or other value after contrast injection Delayed response image (also referred to herein as i-delay) denoting the final contrast enhancement within the sequence of anatomical images, for example, the last image or selected from the last few images.

A multi-channel image representation is created for the sequence of anatomical images. The multi-channel image representation includes the following channels:

Intensity channel including the peak contrast enhanced image (i.e., i-peak).

Contrast-update channel including the computed difference between the peak contrast enhanced image and the pre-contrast image (i.e., i-peak–i-base).

Contrast-washout channel including the computed difference between the initial uptake image and the delayed response image (i.e., i-early–i-delayed).

A trained deep convolutional neural network (CNN) receives the multi-channel image representation as input, and computes an output of a classification category indicative of likelihood of malignancy. For example, the output may include one of the following classification categories: mass, or non-mass. In another example, the output includes one of the following classification categories: malignant lesion, benign lesion, and normal tissue. In yet another example, the output includes a BI-RADS (Breast Imaging-Reporting and Data System) score, or a classification based on one or more BI-RADS scores. BI-RADS is designed as a quality assurance tool by the American College of Radiology (ACR), to make the reporting of breast imaging results more standardized and comprehensible to the non-radiologist reading the report. It is noted that the neural network may output a probability of the accuracy of the classification.

Optionally, the sequence of anatomical images is extracted as two dimensional (2D) slices from three dimensional (3D) image data acquired by an MRI machine executed a T1 weighted protocol of a dynamic contrast enhanced (DCE) study. Each sequence of two dimensional slices may be analyzed by the deep CNN to cover the 3D volume. Alternatively or additionally, the sequence of anatomical images may include projections from orthogonal planes. Alternatively or additionally, the sequence of anatomical images may include 3D images.

Optionally, a patch distinctiveness saliency map is computed for one or more of the images. The patch distinctiveness saliency map may be computed according to a statistical distance between each patch of the image and an average patch along the principal components of the image patches. The patch distinctiveness saliency map is represented as an additional channel of the multi-channel image representation.

Alternatively or additionally, a cross-saliency map is computed for one or more of the images. The cross-saliency map may be computed according to a statistical distance between each patch of one breast and corresponding patch (es) of the contralateral breast. The cross-saliency map is represented as an additional channel of the multi-channel image representation.

Optionally, the patch distinctiveness saliency map and/or the cross-saliency map are analyzed to identify candidate regions that include a relatively higher density of salient values compared to other non-candidate regions. The candidate regions may be detected based on an unsupervised approach. The candidate regions (which may include regions of the other channels corresponding to the candidate regions) may be cropped and fed into the deep CNN for computation of likelihood of malignancy per candidate region. The regions corresponding to the candidate regions may be cropped out from the input of the intensity channel, the contrast-update channel, and the contrast-washout channel, to create a multi-channel representation for each candidate region. The deep CNN may output a binary detection map that includes the candidate regions classified with a classification category indicative of malignancy. Candidate regions that are classified as indicative of likelihood of malignancy may represent a localization of the lesion(s). The binary detection map computed for the patch distinctiveness saliency map may be combined (e.g., via an OR operation) with the binary detection map computed for the cross-saliency map. The binary detection maps (computed per 2D image slice of the sequence) may be added together to generate a projected heatmap indicative of spatial concentration of the candidate regions. The projected heatmap map may be indicative of the location of the detected lesion(s).

Alternatively or additionally, the patch distinctiveness saliency map which is created per image of the sequence may be combined (e.g., adding pixel intensity values of corresponding pixels) to generate a single heat distinctiveness saliency map and/or a single heat cross-saliency map for the sequence of images. Alternatively or additionally, the cross saliency map which is created per image of the sequence may be combined (e.g., adding pixel intensity values of corresponding pixels) to generate a single heat cross-saliency map for the sequence of images. The single heat distinctiveness saliency map and/or the single heat cross-saliency map may be included as one or two additional channels of the multi-channel representation fed as input into the deep CNN. The single heat distinctiveness saliency map and/or the single heat cross-saliency map may be indicative of the location of the detected lesion(s).

An aspect of some embodiments of the present invention relates to systems, an apparatus, methods, and/or code instructions (stored in a data storage device, and executable by hardware processor(s)) for training a deep CNN for detecting an indication of likelihood of malignancy based on a sequence of anatomical images of a target individual. The deep CNN is trained according to a sequence of anatomical images received for each of multiple sample individuals. One or more lesions manually identified within the sequence of anatomical images are manually delineated, for example, by a rectangular bounding box. Each image is associated with a label indicative of the lesion, for example, mass, malignancy, benign. Alternatively or additionally, the label includes a BI-RADS score. Images without lesions may include delineation of normal tissues, and include a label indicative of normal. The multi-channel image representation is computed for each sequence of anatomical images as described herein. The deep CNN is trained according to the multi-channel image representation and associated delineation and associated label.

The multi-channel representation described herein is designed to compactly capture anatomical features, kinetic features, salient features, and/or metabolic features. The multi-channel representation described herein encodes spatial and temporal characteristics of the administered imaging contrast.

The systems, apparatus, methods and/or code instructions (stored in a storage device executed by hardware processor(s)) provided herein provide a technical solution to the technical problem of automatically identifying lesions (which may be malignant) in a sequence of images slices of one or both breasts acquired by a 3D anatomical imaging modality (e.g., MRI). The sequence of images are captured over a period of time during which contrast is administered to the target individual. The total number of images for analysis is quite large, and difficult and/or time consuming for a human radiologist to manually analyze correctly. Automatic classification of lesions in the sequence of images captured over time is a challenging technical problem due to several reasons, for example, small available datasets. In particular, there is a lack of publicly available labeled and/or annotated image sets of one or both breasts that include lesions. Standard automated machine learning methods that rely on large data sets cannot be used due to the lack of available training datasets and due to the fact that such machine learning methods are generally designed for classification of natural images and not of medical images which are different.

Magnetic resonance imaging (MRI) of the breast is a widely-used imaging modality, indicated as a screening examination for women at high risk of breast cancer. A typical breast MRI study consists of 10 to 15 acquired and postprocessed image series, each composed of 50 to 100 two-dimensional (2D) slices, for a total of about 1000-1500 images. Due to this large number of images, reading breast MRI studies and reporting the diagnostic findings is tedious work, time consuming, and prone to human errors, for example, as described with reference to Pages, E. B., Millet, I., Hoa, D., Doyon, F. C., Taourel, P., "Undiagnosed breast cancer at MR imaging: analysis of causes.," Radiology 264(1), 40-50 (2012).

The systems, apparatus, methods and/or code instructions (stored in a storage device executed by hardware processor(s)) provided herein provide a technical solution to the technical problem of providing accurate classification results when large training dataset are unavailable, and small training datasets are available. The systems, apparatus, methods and/or code instructions (stored in a storage device executed by hardware processor(s)) provided herein may be trained to discriminate between benign and malignant lesions using a small training dataset, for example, on the order of a few hundred images (e.g., less than about 500, 1000, 1500, or 2000 images) from a few dozen patients (e.g., less than about 50, 100, 150, 200, or 250 patients).

The systems, apparatus, methods and/or code instructions (stored in a storage device executed by hardware processor(s)) described herein improve performance of a computing device that performs the automatic detection of likelihood of malignancy in the image sequence captured over time. The improvement in performance may be based on an increase in accuracy of detecting the likelihood of malignancy using existing computing resources (e.g., processor(s), and/or data storage), and/or improving the efficiency of detecting the likelihood of malignancy by a reduction in processing time, a reduction in processor utilization, and/or a reduction in data storage requirements. The systems and/or apparatus and/or methods and/or code instructions described herein may train a neural network to perform the classification of a multi-channel image computed from the sequence of images acquired over the time interval using a relatively small sized training set. The neural network is trained relatively quickly due to the small size of the training set and/or due to the multi-channel image data structure. The small sized training set and/or the multi-channel image requires smaller storage capacity in comparison to larger training sets and/or analysis of a large number of individual images. In another example, the trained neural network that classifies the multi-channel image computed from the sequence of images performs the classification within a relatively short processing time, using relatively fewer processing resources, and/or using relatively smaller data storage requirements. The improvement in performance may include training the neural network and/or applying the neural network to the multi-channel image using less memory, and/or using fewer computational resources (e.g., processor(s) utilization), and/or faster computation time, without sacrificing the accuracy (and in many cases improving the accuracy) of the computation of the likelihood of malignancy for.

Moreover, the neural network described herein may be trained relatively quickly with the small training dataset, which is consistent with the recent conclusions of Shin, H.-C., Roth, H. R., Gao, M., Lu, L., Xu, Z., Nogues, I., Yao, J., Mollura, D., Summers, R. M., "Deep Convolutional Neural Networks for Computer-Aided Detection: CNN Architectures, Dataset Characteristics and Transfer Learning.," IEEE Trans. Med. Imaging PP(99), 1 (2016), who studied computer-aided detection problems.

The systems, apparatus, methods and/or code instructions (stored in a storage device executed by hardware processor(s)) described herein improve an underling technical process within the technical field of medical image processing, in particular, within the field of automatic analysis of sequences of anatomical images (e.g., MRI) acquired over a time interval during which contrast is administered to the target individual, to compute a likelihood of malignancy in one or both breasts.

The systems, methods, apparatus, and/or code instructions described herein do not simply perform automation of a manual procedure, but perform additional automated features which cannot be performed manually by a human using pencil and/or paper. The deep CNN described herein automatically extracts features from the multi-channel representation described herein to compute the classification result, which is an entirely different process than that performed by a human interpreter.

The systems, apparatus, methods and/or code instructions (stored in a storage device executed by hardware processor(s)) described herein provide a unique, particular, and advanced technique of analyzing sequences of anatomical images of one or both breasts (e.g., MRI images) acquired over a time interval during which contrast is administered, by computing a multi-channel image from the sequence of anatomical images, and computing the likelihood of malignancy within the sequence of anatomical images by a neural network that analyses the multi-channel image. The systems and/or methods described herein provide a unique, particular, and advanced technique of creating a trained neural network that computes likelihood of malignancy within the sequence of anatomical images by analysis of the multi-channel image computed from the images of the sequence of anatomical images.

The systems, apparatus, methods and/or code instructions (stored in a storage device executed by hardware processor(s)) described herein generate new data in the form of the multi-channel image and/or in the form of the trained neural network that analyzes the multi-channel image.

The systems, apparatus, methods and/or code instructions (stored in a storage device executed by hardware processor(s)) described herein are tied to physical real-life components, for example, anatomical image machine (e.g., MRI machine) that captures the sequence of anatomical images over the time interval, and computational hardware (e.g., hardware processor(s), physical memory device(s)) that stored data and/or analyze the multi-channel image.

Accordingly, the systems, apparatus, methods and/or code instructions (stored in a storage device executed by hardware processor(s)) described herein are inextricably tied to computer technology and/or physical components (e.g., MRI machine, hardware processor(s), storage device(s)) to overcome an actual technical problem arising in processing and/or analysis of anatomical images to detect breast cancer.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/ or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Automated processing of breast MRI has been previously suggested for breast segmentation, for example, as described with reference to Gubern-Mérida, A., Kallenberg, M., Mann, R. M., Martí, R., Karssemeijer, N., "Breast segmentation and density estimation in breast MRI: a fully automatic framework.," IEEE J. Biomed. Heal. iformatics 19(1), 349-357 (2015), and Wu, S., Weinstein, S. P., Conant, E. F., Schnall, M. D., Kontos, D., "Automated chest wall line detection for whole-breast segmentation in sagittal breast MR images.," Med. Phys. 40(4), 042301 (2013), lesion detection, for example, as described with reference to Chang, Y.-C., Huang, Y.-H., Huang, C.-S., Chen, J.-H., Chang, R.-F., "Computerized breast lesions detection using kinetic and morphologic analysis for dynamic contrast-enhanced MRI.," Magn. Reson. Imaging 32(5), 514-522 (2014), Renz, D. M., Böttcher, J., Diekmann, F., Poellinger, A., Maurer, M. H., Pfeil, A., Streitparth, F., Collettini, F., Bick, U., et al., "Detection and classification of contrast-enhancing masses by a fully automatic computer assisted diagnosis system for breast MRI.," J. Magn. Reson. Imaging 35(5), 1077-1088 (2012), and lesion classification, for example, as described with reference to Gallego-Ortiz, C., Martel, A. L., "Improving the Accuracy of Computer-aided Diagnosis for Breast MR Imaging by Differentiating between Mass and Nonmass Lesions.," Radiology, 150241 (2015), Agliozzo, S., De Luca, M., Bracco, C., Vignati, A., Giannini, V., Martincich, L., Carbonaro, L. A., Bert, A., Sardanelli, F., et al., "Computer-aided diagnosis for dynamic contrast-enhanced breast MRI of mass-like lesions using a multiparametric model combining a selection of morphological, kinetic, and spatiotemporal features.," Med. Phys. 39(4), 1704-1715 (2012), Agner, S. C., Soman, S., Libfeld, E., McDonald, M., Thomas, K., Englander, S., Rosen, M. A., Chin, D., Nosher, J., et al., "Textural kinetics: a novel dynamic contrast-enhanced (DCE)-MRI feature for breast lesion classification.," J. Digit. Imaging 24(3), 446-463 (2011), Pang, Z., Zhu, D., Chen, D., Li, L., Shao, Y., "A computer-aided diagnosis system for dynamic contrast enhanced MR images based on level set segmentation and ReliefF feature selection" Comput. Math. Methods Med. 2015, 450531 (2015). These may be broadly categorized into: image processing approaches, for example, as described with reference to Vignati, A., Giannini, V., et al.: A fully automatic lesion detection method for DCE-MRI fatsuppressed breast images, 26 Feb. 2009 2. Ertas, G., Doran, S., Leach, M. O.: Computerized detection of breast lesions in multi-centre and multi-instrument DCE-MR data using 3D principal component maps and template matching. Phys. Med. Biol. 56, 7795-7811 (2011) 3. McClymont, D., Mehnert, A., et al.: Fully automatic lesion segmentation in breast MRI using mean-shift and graph-cuts on a region adjacency graph. J. Magn. Reson. Imaging 39, 795-804 (2014), machine learning approaches, for example, as described with reference to Gallego-Ortiz, C., Martel, A. L.: Improving the accuracy of computer-aided diagnosis for breast MR imaging by differentiating between mass and nonmass lesions. Radiology 278, 679-688 (2016), Agner, S. C., Soman, S., et al.: Textural kinetics: a novel dynamic contrast-enhanced (DCE)-MRI feature for breast lesion classification. J. Digit. Imaging 24, 446-463 (2011), or a combination of both, for example, as described with reference to Ertaw, G., Gülçër, H. Ö., et al.: Breast MR segmentation and lesion detection with cellular neural networks and 3D template matching. Comput. Biol. Med. 38, 116-126 (2008), Renz, D. M., Böttcher, J., et al.: Detection and classification of contrast-enhancing masses by a fully automatic computer-assisted diagnosis system for breast MRI. J. Magn. Reson. Imaging 35, 1077-1088 (2012), Pang, Z., Zhu, D., Chen, D., Li, L., Shao, Y.: A computer-aided diagnosis system for dynamic contrast-enhanced MR images based on level set segmentation and ReliefF feature selection. Comput. Math. Methods Med. 2015(2015), Article ID 450531 (2015). However, such previous lesion classification methods are based on hand-crafted features for differentiation between malignant and benign findings. Such hand-crafted features may be difficult to define (e.g., require expert knowledge) and/or may not be fully accurate, since other extracted features may be missed. In contrast, the systems, methods, apparatus, and/or code instructions described herein are based on features that are automatically identified and extracted by a neural network, which are different than the hand crafted features.

Deep convolutional neural networks (CNN), which automatically learn image features, have become the state-of-the-art technique for natural image classification. However, medical images are different than natural image classification. In the medical imaging domain, CNN have been attempted to be used for example, for abnormality detection, for example, as described with reference to Roth, H., Lu, L., Liu, J., Yao, J., Seff, A., Cherry, K., Kim, L., Summers, R., "Improving Computer-aided Detection using Convolutional Neural Networks and Random View Aggregation.," IEEE Trans. Med. Imaging PP(99), 1 (2015), segmentation, for example, as described with reference to Neeraj Dhungel, Gustavo Carneiro, A. P. B., "Deep Learning and Structured Prediction for the Segmentation of Mass in Mammograms," Med. Image Comput. Comput. Interv.—MICCAI 2015, 605-612, Springer International Publishing (2015), and classification, for example, as described with reference to Arevalo, J., González, F. A., Ramos-Pollán, R., Oliveira, J. L., Guevara Lopez, M. A., "Representation learning for mammography mass lesion classification with convolutional neural networks," Comput. Methods Programs Biomed. (2016), Hua, K.-L., Hsu, C.-H., Hidayati, S. C., Cheng, W.-H., Chen, Y.-J., "Computer-aided classification of lung nodules on computed tomography images via deep learning technique.," Onco. Targets. Ther. 8, 2015-2022 (2015). However, applying CNN techniques to medical images is challenged by two technical problems compared to natural images: (1) the amount of training medical images is typically small in comparison to training using natural images, and (2) there are no available domain-specific pre-trained models that may be used without retraining the neural network. Although non-medical pre-trained models have been applied to represent and classify medical images Bar, Y., Diamant, I., Wolf, L., Greenspan, H., "Chest Pathology Detection Using Deep Learning With Non-Medical Training," IEEE Int. Symp. Biomed. Imaging, 2-5 (2015), such models trained on natural images are not optimal for medical images. The medical images are typically gray-level, low-contrast, and texture-rich. Moreover, retraining deep network architectures using a small data set may not always converge to an optimal solution.

Gallego-Ortiz et al. reported an AUROC of 0.91 in differentiating mass from non-mass lesions in breast-MR, using a set of 176 hand-crafted features and a two-stage cascade classifier. Pang et al. used texture and morphology features with SVM classifier to achieve an accuracy of 0.9 in discriminating benign and malignant breast lesions. The experimental results (described below with reference to the "Examples" section) achieved by implementing the systems, apparatus, methods, and/or code instructions described herein are comparable to the above cited references, while advantageously using the raw images and automatically extracting the discriminative features in comparison to the cited references.

The CNN trained according to the systems, methods, apparatus, and/or code instructions described herein provides superior results in comparison to feature extraction from non-medical models. Feature extraction from non-medical models is also much less robust to the size of the training data. Inventor hypothesize that the underlying reason for the observation of the superiority of the CNN described herein may be that the mapping between the raw image pixels and the feature vectors used for classification is much more complex in the alternative pre-trained cases, requiring a large training set for good generalization. Conversely, the designated CNN described herein may create a more optimal feature representation, which is sufficiently robust to training data reductions.

It is noted that deep convolutional neural networks (CNN) applied to breast MRI images for mass calcification as part of an automated lesion segmentation pipeline as described with reference to Wu, H., Cristina Gallego-Ortiz, A. M.: Deep artificial neural network approach to automated lesion segmentation in breast DCE-MRI. In: Proceedings of the 3rd MICCAI Workshop on Breast Image Analysis, pp. 73-80 (2015). Such CNNs received a single image as input, which is in contrast to the multi-channel representation described herein that provides improved classification results.

It is noted that the majority of published work on lesion detection in breast MRI uses proprietary datasets, typically small in size, which could not be used as a common benchmark for comparison. The reported results show a large variability in sensitivity and false positive rate, ranging from 1 to 26 false positives per study at a sensitivity range of 0.89 to 1.0, for example, to Viganti, A. et al., Ertas G., et al, Wu, H., et al., An objective performance comparison between methods requires publicly available large datasets with ground-truth annotations. In the experiments described below, MRI studies from the TCIA repository were used, as described with reference to Clark, K., Vendt, B., et al.: The Cancer Imaging Archive (TCIA): maintaining and operating a public information repository. J. Digit. Imaging. 26, 1045-1057 (2013), enriched by additional proprietary studies.

Figure 2:
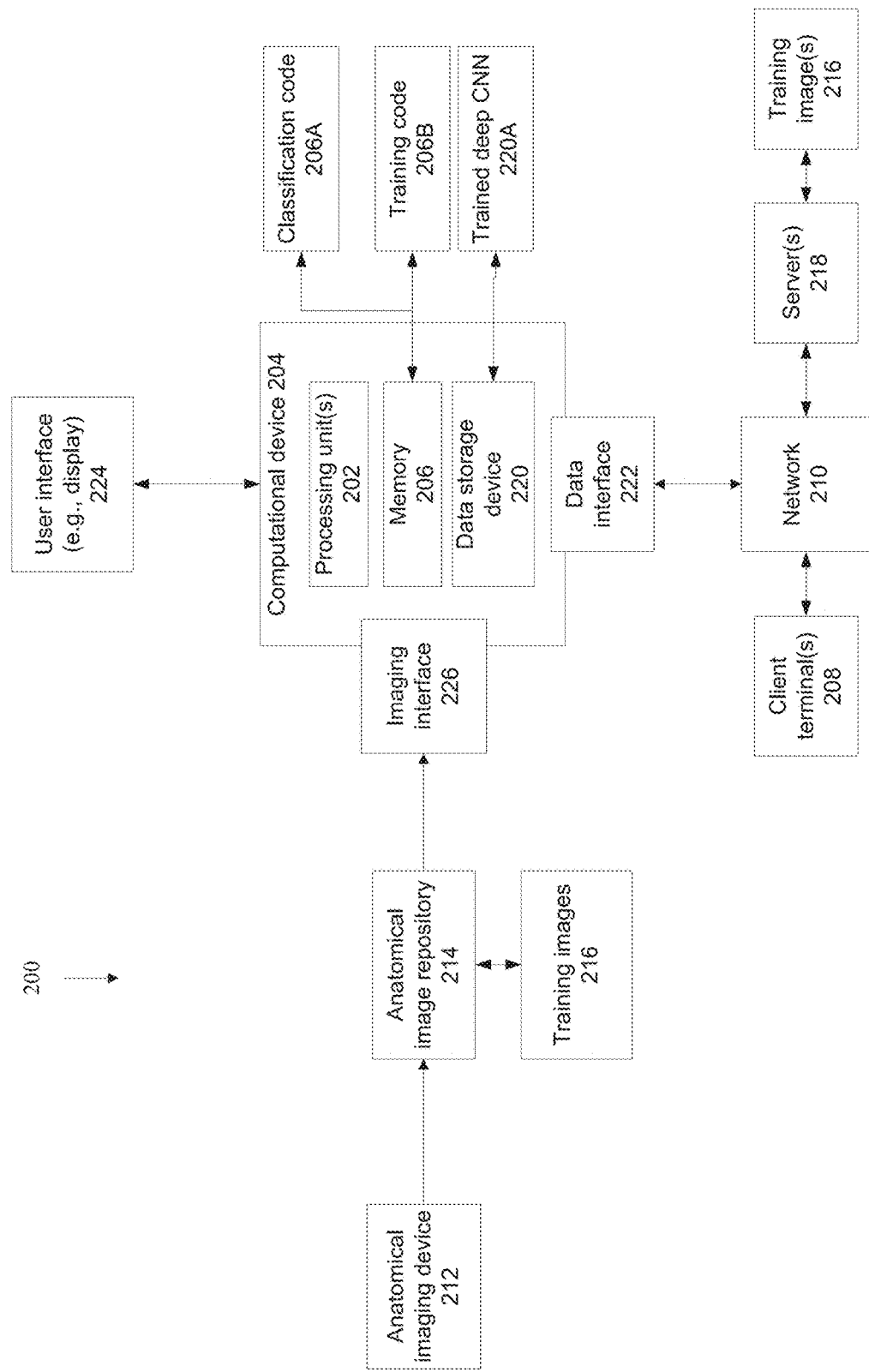
FIG. 2 is a block diagram of components of a system that computes the indication of likelihood of malignancy by a trained deep convolutional neural network that receives the multi-channel image computed from a sequence of anatomical images, in accordance with some embodiments of the present invention.
Figure 3:
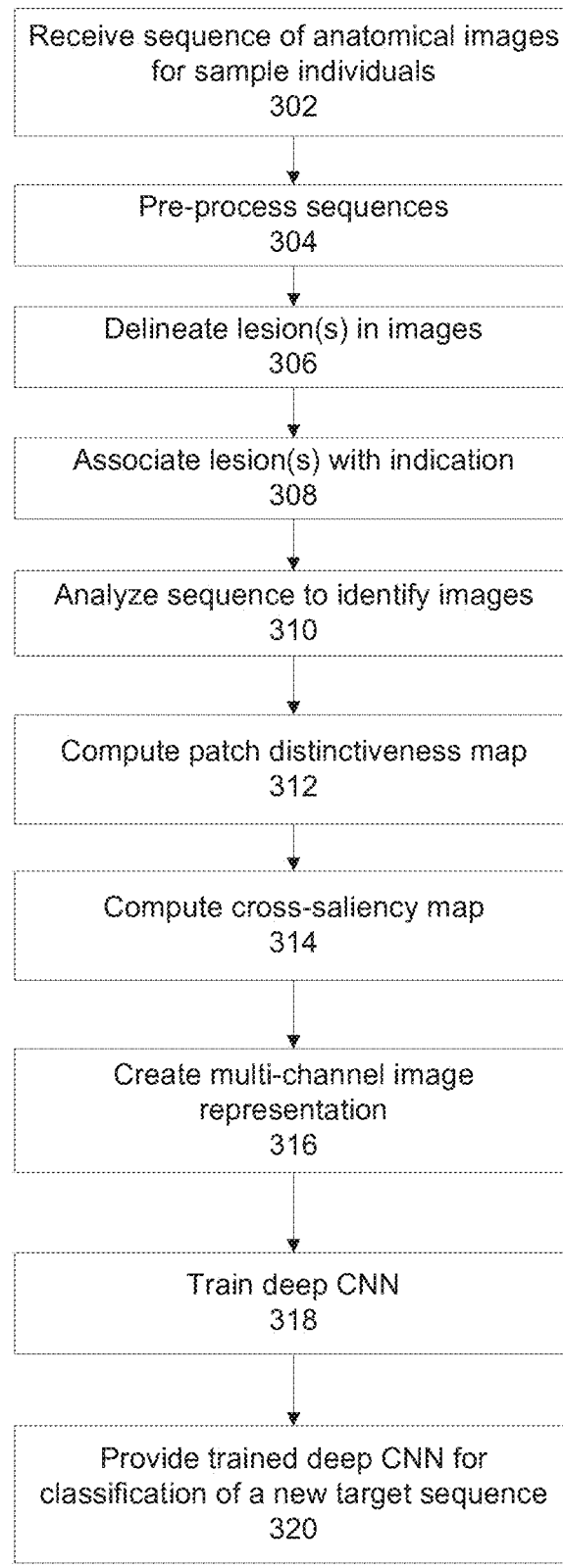
FIG. 3 is a flowchart of a method of training the deep convolutional neural network for computing the likelihood of malignancy according to the multi-channel image computed from the sequence of anatomical images, in accordance with some embodiments of the present invention.

Reference is now made to FIG. 1, which is a flowchart of a method for computing an indication of likelihood of malignancy in one or both breasts of a target individual by a trained deep convolutional neural network according to a computed multi-channel image, in accordance with some embodiments of the present invention. Reference is also made to FIG. 2, which is a block diagram of components of a system 200 that computes the indication of likelihood of malignancy by a trained deep convolutional neural network that receives the multi-channel image computed from a sequence of anatomical images, in accordance with some embodiments of the present invention. System 200 may implement the features of the method described with reference to FIG. 1, by one or more hardware processors 202 of a computing device 204 executing code instructions stored in a memory (also referred to as a program store) 206. Reference is also made to FIG. 3, which is a flowchart of a method of training the deep convolutional neural network for computing the likelihood of malignancy according to the multi-channel image computed from the sequence of anatomical images, in accordance with some embodiments of the present invention. Components of system 200 may be used to train the deep neural network.

Computing device 204 may be implemented as, for example, a client terminal, a server, a radiology workstation, a virtual machine, a virtual server, a computing cloud, a mobile device, a desktop computer, a thin client, a Smartphone, a Tablet computer, a laptop computer, a wearable computer, glasses computer, and a watch computer. Computing device 204 may include locally stored software that executes one or more of the acts described with reference to FIG. 1 and/or FIG. 3, and/or may act as one or more servers (e.g., network server, web server, a computing cloud) that provides services (e.g., one or more of the acts described with reference to FIG. 1 and/or FIG. 3) to one or more client terminals 208 (e.g., remotely located radiology workstations) over a network 210, for example, providing software as a service (SaaS) to the client terminal(s) 208, providing an application for local download to the client terminal(s) 208, and/or providing functions using a remote access session to the client terminals 208, such as through a web browser.

Computing device 204 receives a sequence of anatomical images captured by an anatomical imaging device(s) 212, for example, a magnetic resonance imaging (MRI) device, an x-ray based mammogram imaging device, and/or a breast tomosynthesis device. Sequence(s) of anatomical images captured by anatomical imaging device 212 may be stored in an anatomical image repository 214, for example, a storage server, a computing cloud, a virtual memory, and a hard disk. The sequences of anatomical images stored by anatomical image repository 214 may include sequence(s) of anatomical images of one or more target patients for analysis, and/or training images 216 that have been previously analyzed (e.g., by radiologists) and labeled with findings indicative of, for example, malignancy, benign lesion, and/or normal tissue. Training images 216 are used to train the neural network, as described herein. It is noted that training images 216 may be stored by a server 218, accessible by computing device 204 over network 210, for example, a publicly available training dataset available from The Cancer Imaging Archive (TCIA), as described with reference to Clark K. et al.

Computing device 204 may receive the sequence(s) of anatomical image(s) via one or more imaging interfaces 226, for example, a wire connection (e.g., physical port), a wireless connection (e.g., antenna), a network interface card, other physical interface implementations, and/or virtual interfaces (e.g., software interface, application programming interface (API), software development kit (SDK), virtual network connection).

Memory 206 stores code instructions executable by hardware processor(s) 202. Exemplary memories 206 include a random access memory (RAM), read-only memory (ROM), a storage device, non-volatile memory, magnetic media, semiconductor memory devices, hard drive, removable storage, and optical media (e.g., DVD, CD-ROM). For example, memory 206 may store classification code instructions 206A that execute one or more acts of the method described with reference to FIG. 1, and/or training code instructions 206B that execute one or more acts of the method described with reference to FIG. 3.

Computing device 204 may include a data storage device 220 for storing data, for example, a trained neural network 220A for computing likelihood of malignancy according to a multi-channel image computed from a sequence of anatomical images. Data storage device 220 may be implemented as, for example, a memory, a local hard-drive, a removable storage unit, an optical disk, a storage device, a virtual memory and/or as a remote server 218 and/or computing cloud (e.g., accessed over network 210). It is noted that neural network 220A may be stored in data storage device 220, for example, with executing portions loaded into memory 206 for execution by processor(s) 202.

Computing device 204 may include data interface 222, optionally a network interface, for connecting to network 210, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing device 204 may access one or more remote servers 218 using network 210, for example, to download updated training images 216.

Computing device 204 may connect using network 210 (or another communication channel, such as through a direct link (e.g., cable, wireless) and/or indirect link (e.g., via an intermediary computing unit such as a server, and/or via a storage device) with one or more of:

Client terminal(s) 208, for example, when computing device 204 acts as a server providing services (e.g., SaaS) to remote radiology terminals, by analyzing remotely obtained sequences of anatomical images (and/or analyzing the multi-channel image computed from the sequence(s) of anatomical images) for computing the likelihood of malignancy in one or both breasts.

Server 218, for example, when server 218 is part of picture archiving and communication system (PACS), which may storage large numbers of sequences of anatomical images for analysis, for example, captured by an MRI of a radiology clinic.

Anatomical image repository 214 that stores sequences of anatomical images.

Computing device 204 includes or is in communication with a user interface 224 that includes a mechanism designed for a user to enter data (e.g., patient data) and/or view the classification result and/or view the computed multi-channel image. Exemplary user interfaces 224 include, for example, one or more of, a touchscreen, a display, a keyboard, a mouse, and voice activated software using speakers and microphone.

Referring now to FIG. 1, at 102, a sequence of anatomical images is received. The sequence is received by computing device 204 via imaging interface 226, for example, from anatomical imaging device 212 and/or anatomical image repository 214.

The sequence of anatomical images capture at least a portion of one or both breasts of a target individual. The sequence of anatomical images are acquired over a time interval during which contrast is administered to the target individual, including at least one image when no contrast is administered. The time interval spans over, for example, about 2-5 minutes, or other periods of time, for example, depending on the ability of the contrast to diffuse through the body of the target individual.

Optionally, one or more sequence of anatomical images are extracted from 3D image data. Each sequence is extracted as 2D slices from the 3D image data, for example, to cover the volume of one or both breasts. The 2D slices may be projections of the 3D image data, and/or slices through the 3D image data.

Optionally, the 3D image data acquired by an MRI machine executed a T1 weighted protocol of a dynamic contrast enhanced (DCE) study. It is noted that the deep CNN described herein may analyze previously acquired DCE T1 MRI image, for example, stored in a PACS server.

It is noted that the 2D images and/or 3D image data may be acquired by other imaging modalities, for example, x-ray based modalities, for example, a mammogram device, a breast tomosynthesis device, and/or ultrasound images acquired by one or more ultrasound transducers.

At 104, the sequence of anatomical images may be pre-processed.

Optionally, the pre-processing includes an operation(s) for alignment and/or registration of the anatomical images of the sequence, for example, along a longitudinal axis. The alignment and/or registration may enable accurate addition and/or subtraction of images.

Alternatively or additionally, the pre-processing includes a process for normalization of intensity values of the anatomical images of the sequence and/or setting the standard deviation of the intensity values to a unit (e.g., one) The normalization of intensity values defines a relatively measure between the images, taking into account contrast administration, and wash-out of the contrast. The normalization may be performed, for example, by computing a total intensity value for each image, an average intensity value for each image, a normalized intensity value for each image, and/or a relative intensity value for each image. The values of the normalized images may be graphed, stored in an array, and/or other data structures. The values of the normalized images are analyzed to identify the images from the sequence for computation of the channels of the multi-channel representation.

Alternatively or additionally, the pre-processing includes a process for segmentation of the breast tissue from the images of the sequence.

At 106, the sequence of anatomical images is analyzed to identify the following images. The images may be identified according to a relative intensity value Baseline pre-contrast image (also referred to herein as i-base) denoting lack of contrast within the sequence of anatomical images. The i-base image may be identified, for example, as the first image of the sequence, and/or the image associated with the lowest relative intensity value.

Peak contrast enhanced image (also referred to herein as i-peak) denoting a peak contrast enhancement of the sequence of anatomical images. The i-peak image may be identified, for example, as the image with the highest relative intensity value, and/or the peak of the generated graph.

Initial uptake image (also referred to herein as i-early) denoting initially detectable contrast within the sequence of anatomical images. The i-early image may be identified, for example, as the image with an intensity value above the intensity of the i-base image, for example, according to a threshold designed to exclude intensity variations due to noise and/or artifacts.

Delayed response image (also referred to herein as i-delay) denoting one of the last portion of images of the sequence of anatomical images. The i-delay image may be selected as the last image of the sequence, and/or the image representing an elapsed time (e.g., 2 minutes) from the time associated with the i-peak image.

Optionally, at 108, a patch distinctiveness saliency map is computed.

The patch distinctiveness saliency map may be computed according to a statistical distance (e.g., L1-distance) between each patch of a certain image of the sequence of anatomical images, and an average patch along the principal components of the image patches of the certain image, for example, as described with reference to Margolin, R., Tal, A., Zelnik-Manor, L.: What makes a patch distinct? In: 2013 IEEE Conference on Computer Vision and Pattern Recognition, pp. 1139-1146. IEEE (2013).

For a certain vectorized patch $p_{x,y}$ around the points (x,y), the patch distinctiveness may be mathematically represented as:

$$PD(p_{x,y}) = \Sigma_{k=1}^{n} |p_{x,y} \omega_k^T|$$

Where:
PD denotes the patch distinctiveness,
$p_{x,y}$ denotes the vectorized patch around the points (x,y),
$\omega^T_k$ denotes the kth principal component of the entire image patch distribution.

The patch distinctiveness saliency map may be computed for one or more images of the sequence, optionally for each image of the sequence. The patch distinctiveness saliency maps may be summed (e.g., values of corresponding pixels are added together) to create a heat map having values denoting a degree of saliency.

The patch distinctiveness saliency heatmap may be included as an additional channel of the multi-channel representation fed as input into the deep CNN. The patch distinctiveness saliency heatmap may be indicative of the location of the detected lesion(s), for example, peak intensity point(s) of the heatmap associated with a multi-channel image representation classified as an indication of lesion and/or malignancy may be indicative of the location of the lesion and/or malignancy.

Optionally, at 110, a cross-saliency map is computed. The cross saliency includes, for each patch of one breast, the corresponding nearest neighbor patch in the contralateral breast. The cross-saliency map stores cross-saliency values indicative of the distinctiveness of each patch.

The cross-saliency map may be computed according to a statistical distance between a certain patch of one breast of a certain image of the sequence of anatomical images, and corresponding patches of the contralateral breast of the same image.

The cross-saliency map may be computed by computing a contralateral patch flow according to a flow field between patches of left and right breasts. The flow field may be computed, for example, according to the PatchMatch algorithm described with reference to Barnes, C., Shechtman, E., Goldman, D. B., Finkelstein, A.: The generalized PatchMatch correspondence algorithm. In: Daniilidis, K., Maragos, P., Paragios, N. (eds.) ECCV 2010. LNCS, vol. 6313, pp. 29-43. Springer, Heidelberg (2010). The flow field identifies for each patch of one breast the corresponding nearest neighbor patch in the contralateral breast.

The flow field may be computed based on the smooth motion field assumption for computation of a dense flow field for each pixel by considering a k×k patch around the respective pixel. Initially, for each pixel location denoted (x,y), a random displacement vector (denoted T) is assigned. The random displacement vector marks a location of a corresponding patch in the contralateral breast. A quality of the displacement vector is measured according to a computed distance (e.g., L2 distance) between the certain patch of one breast and the corresponding patch of the contralateral breast. The quality of the displacement vector T may be computed according to the following mathematical relationship:

$$D(p_{x,y}, p_{x+T_x, y+T_y}) = \sum_{i=x-k/2}^{x+k/2} \sum_{j=y-k/2}^{y+k/2} \|I(i,j) - I(i+T_x, j+T_y)\|_2$$

where:
k denotes a dimension of the patch around the respective pixel,
$p_{x,y}$ denote the respective pixel at coordinates (x,y),
T denotes the displacement vector,
I denotes a patch,
D denotes the quality measure.

An attempt at improvement in displacement of a certain patch of the one breast is performed according to displacement vectors of neighboring patches of the contralateral breast. The improvement of displacement is based on testing new hypothesis generated from the displacement vectors of neighboring patches in the same image. Iterations are performed between the assignment of the random displacement vector and improvement in displacement. The location of the best corresponding patch of the contralateral breast according to the statistical distance. is stored.

The cross-saliency value of the cross-saliency map of each patch is estimated according to an error of the nearest neighbor patch. The nearest neighbor error (denoted NNE) may be computed based on the following mathematical relationship:

$$NNE(p_{x,y}) = \min_{T} D(p_{x,y}, p_{x+T_x, y+T_y})$$

$p_{x,y}$ denote the respective pixel at coordinates (x,y),
T denotes the displacement vector,
D denotes the quality measure,
NNE denotes the nearest neighbor error measure.

The cross-saliency map may be computed for one or more images of the sequence, optionally for each image of the sequence. The cross-saliency maps may be summed (e.g., values of corresponding pixels are added together) to create a heat map having values denoting a degree of saliency.

The cross-saliency heatmap may be included as an additional channel of the multi-channel representation fed as input into the deep CNN. The cross-saliency heatmap may be indicative of the location of the detected lesion(s), for example, peak intensity point(s) of the heatmap associated with a multi-channel image representation classified as an indication of lesion and/or malignancy may be indicative of the location of the lesion and/or malignancy.

At 112, the patch distinctiveness saliency map of one or more images, and/or the cross-saliency map of one or more images, and/or the patch distinctiveness heat map, and/or the cross-saliency map heat map, are analyzed to identify candidate region(s) that include a relatively higher density of salient values compared to non-candidate regions. The analysis may be performed, for example, based on a scale-invariant code that searches for regions with high density of salient values.

The candidate regions may be detected based on an unsupervised approach.

The candidate regions detected for each slice may be cropped from the slice image by a bounding region (e.g., square and/or rectangular boxes). Exemplary window sizes are the range of 5 to 50 pixels and normalized threshold values from 0.3 to 0.9. Bounding boxes may be extended for example, by 20% to ensure that the entire lesion is included in the cropped image. The extracted lesion images may be resized according to the input of the deep CNN.

For a given range of window sizes denoted ($w_i$, $h_j$) and a set of threshold values {$t_1, t_2, \ldots t_n$}, for each pixel denoted (x,y) and a region denoted $s_{x,y}$ of size denoted $w_i \times h_j$ around it, the following mathematical relationship is evaluated:

$$\text{Score}(x, y) = \max_{w_i h_j t_k} \frac{\sum (s_{x,y} > t_k)}{w_i \cdot h_j} \sum s_{x,y}$$

Where Score (x,y) denotes a score value computed for the pixel at (x,y). A score image is generated from the set of score values computed for each of the pixels.

Non-maximal suppression may be applied to the score image to obtain the locations of local maxima. Exemplary window sizes are in the range of 5-50 pixels, and normalized threshold values from 0.3-0.9. A binary detection mask is created that includes the candidate regions indicative of the locations of local maxima.

Optionally, the detection map is created for each patch distinctiveness saliency map of one or more images, and/or the cross-saliency map of one or more images, and/or the patch distinctiveness heat map, and/or the cross-saliency map.

The detection maps may be combined into a single detection map, for example, by an OR operation.

Optionally, the candidate regions are cropped from the at least one image. Each cropped candidate region is resized according to the input of the deep CNN. The deep CNN computes a classification category indicative of likelihood of malignancy for each of the candidate regions. The cropped candidate regions may serve as the patch distinctiveness saliency map and/or the cross-saliency map that are fed into respective channels of the multi-channel image representation, as described with reference to act 114.

Optionally, the candidate regions are cropped such that each channel of the multi-channel image representation includes a region(s) corresponding to the candidate region(s).

At 114, a multi-channel image representation is computed. The multi-channel image representation includes at least the following three channels:
Intensity channel including the peak contrast enhanced image (i.e., i-peak).
Contrast-update channel including the computed difference between the peak contrast enhanced image and the pre-contrast image (i.e., i-peak–i-base).
Contrast-washout channel including the computed difference between the initial uptake image and the delayed response image (i.e., i-early–i-delayed).

Optionally, 32×32×5 multi-channel images may be created with 3 channels of the DCE image and 2 channels of the corresponding saliency maps.

Figure 4:
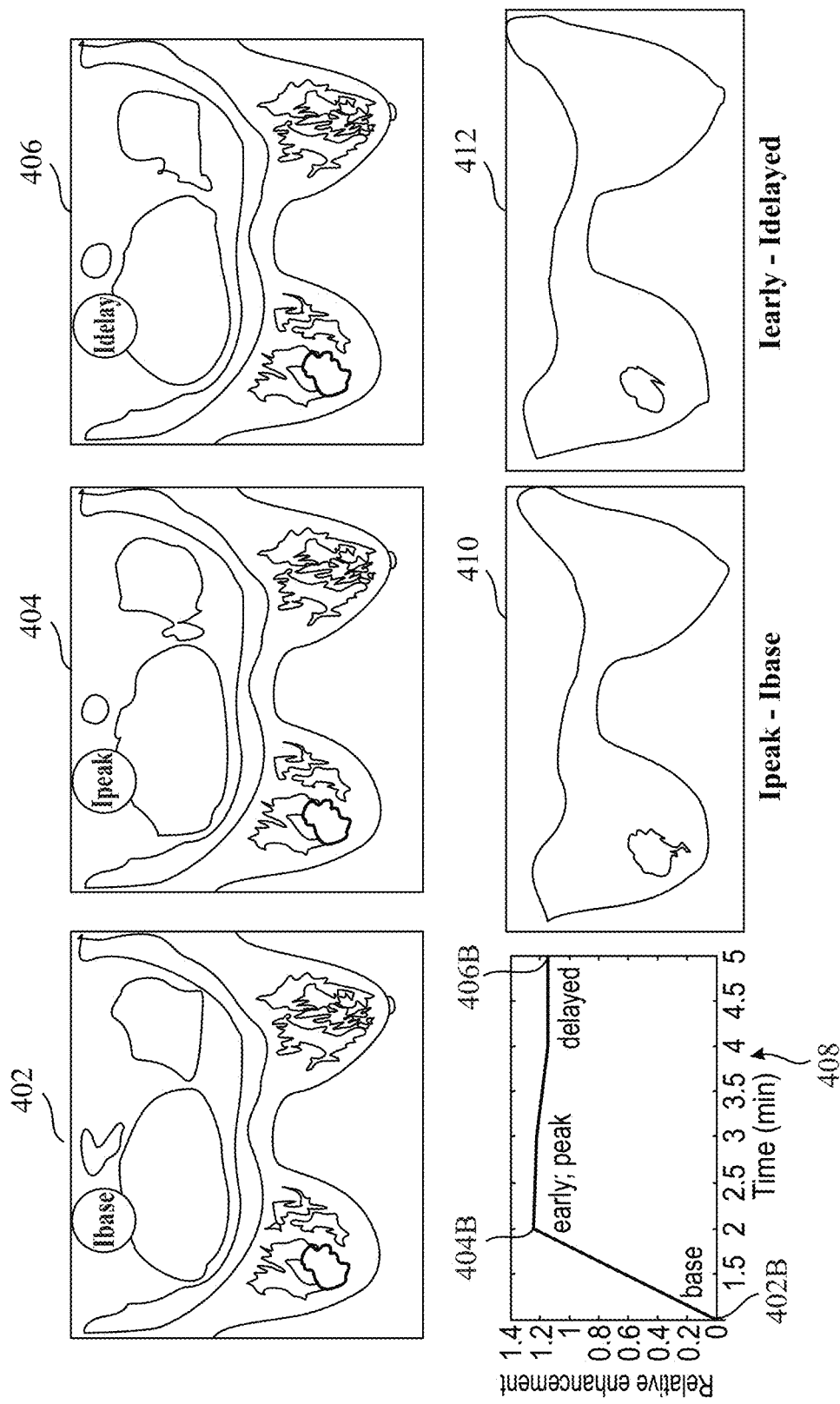
FIG. 4 is a schematic depicting an example of the three channels of the multi-channel image and the images used to compute the three channels, in accordance with some embodiments of the present invention.

Reference is now made to FIG. 4, which is a schematic depicting an example of the three channels of the multi-channel image and the images used to compute the three channels, in accordance with some embodiments of the present invention. The channels of the multi-channel image were computed from a sequence of axial DCE T1 MRI images. Image 402 denotes the baseline image acquired before contrast administration (i.e., i-base). Image 404 denotes the image acquired during peak contrast (i.e., i-peak). Image 406 denotes the image acquired after contrast washout (i.e., i-delayed). Graph 408 denotes the value of the computed intensity (e.g., total intensity, average intensity, normalized (i.e., relative) intensity) computed per image of the sequence, captured at different times. Graph 408 denotes the pattern of contrast uptake and the temporal location of each sequence. Images 402, 404, and 406 may be selected according to corresponding points 402B, 404B, and 406B on graph 408. The multi-channel image includes images 410 and 412. Image 410 is computed as the difference between images 404 and 402 (i.e., i-peak–i-base). Image 412 is computed as the difference between an early contrast washout image (i.e., i-early, not shown) and image 406 (i.e., i-early–i-delayed).

Referring now back to act 114 of FIG. 1, the multi-channel image representation may include one or both of the following channels:
Patch distinctiveness saliency channel that includes the patch distinctiveness saliency map, for example, the patch distinctiveness saliency heatmap, and/or candidate region(s).
Cross-saliency channel that includes the cross-saliency map, for example, the cross-saliency heatmap, and/or candidate region(s).

At 116, the multi-channel image representation is provided as input to the trained deep CNN for computation of one or more classification categories indicative of likelihood of malignancy. It is noted that the classifications indicative of likelihood of malignancy may include classifications for which the likelihood of malignancy is low, for example, benign lesion, and normal tissue. Exemplary classification categories indicative of likelihood of malignancy include: {mass, no mass}, {malignancy, benign}, {suspicious, normal}, a value of the BI-RADS score, and/or a classification category that includes two or more BI-RADS scores.

The deep CNN is trained as described with reference to FIG. 3.

Optionally, the trained deep neural network includes nine convolutional layers in three consecutive blocks. The first block may include two 5×5×32 filters with ReLU layers followed by a max pooling layer. The second block may include four 5×5×32 filters with ReLU layers flowed by an average pooling layer. The third block may include three convolutional layers of size 5×5×64, 6×6×64, and 3×3×64, where each of the three convolutional layers is followed by a ReLU. The trained deep CNN may be terminated by a fully connected layer with 128 neurons and a softmax loss layer.

Optionally, at 118, one or more lesion detection maps are computed based on the output of the deep CNN.

The deep CNN may output a binary detection map that includes the candidate regions computed with the classification category indicative of likelihood of malignancy for each of the candidate regions.

Optionally, the values of the binary detection maps generated for each image of the sequence of anatomical images are summed along a longitudinal axis, to generate a projected heatmap indicative of spatial concentration of candidate regions.

Optionally, a threshold is applied to the projected heatmap to generate a thresholded heatmap indicative of a further rejection of false detections.

At 120, the output of the CNN and/or the lesion detections maps are provided, for example, presented on a display (e.g., as a pop-up message, and/or blinking light and/or other representation), stored in a data storage device (e.g., within the patient electronic medical record), and/or forwarded to another server (e.g., to a PACS server for digital annotation of the sequence of images).

The heatmap may be indicative of the location of the detected lesion.

Figure 5:
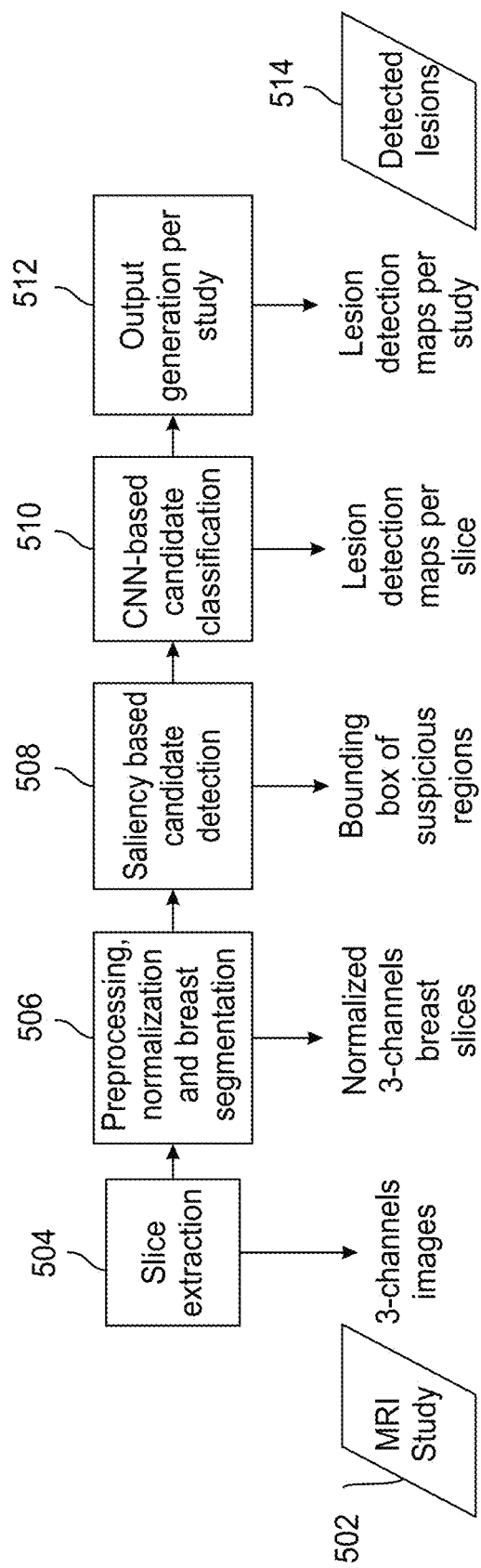
FIG. 5 is a dataflow diagram depicting dataflow for computing likelihood of malignancy based on a multi-channel image representation and processed by a trained convolutional neural network, in accordance with some embodiments of the present invention.

Reference is now made to FIG. 5, which is a dataflow diagram depicting dataflow for computing likelihood of malignancy based on a multi-channel image representation computed from a sequence of anatomical images capturing contrast administration and processed by a trained convolutional neural network, in accordance with some embodiments of the present invention. The dataflow described with reference to FIG. 5 may be based on the method described with reference to FIG. 1 and/or implemented by components of system 200 described with reference to FIG. 2. At 502, the sequence(s) of anatomical images (e.g., MRI) is acquired, for example, as 3D image data. At 504, a set of 2D image slices are acquired from each sequence. At 506, the sequence(s) are optionally pre-processed (e.g., as described with reference to act 104 of FIG. 1) and/or analyzed to identify images for computation of the channels of the multi-channel image (e.g., as described with reference to act 106 of FIG. 1). At 508, patch distinctiveness saliency map(s) and/or cross-saliency map(s) are computed (e.g., as described with reference to acts 108-110 of FIG. 1). The map(s) are analyzed to identify candidate regions(s) (e.g., as described with reference to act 112 of FIG. 1). At 510, the deep CNN classifies the multi-channel image representation (e.g., as described with reference to acts 114-118 of FIG. 1). At 512, the output is provided (e.g., as described with reference to act 112 of FIG. 1). At 514, the detected lesions may be further processed, for example, manually analyzed by a radiologist and/or undergo additional processing by code.

Reference is now made to FIG. 3, which is a flowchart of a method of training a deep CNN for detecting an indication of likelihood of malignancy according to a multi-channel image representation computed from a sequence of anatomical images, in accordance with some embodiments of the present invention.

At 302, training images are received for sample individuals. The training images may be stored, for example, as training images 216 in anatomical image repository 214, and/or by server(s) 218 (e.g., PACS server, medical record server). Each set of training images includes a sequence of anatomical images, for example, as described with reference to act 102 of FIG. 1.

At 304, the training image may be pre-processed, for example, as described with reference to act 104 of FIG. 1.

The training images may be augmented to increase the size of the training dataset, for example, by shifting regions of interest, adding one or more rotations (e.g., 90°, 180°, 270°) and/or adding one or more flipping (e.g., left-right, up-down) variants, for each image.

At 306, a sub-set of images of each sequence that include at least one lesion are manually delineated to define the boundaries of the lesion. The delineation may be performed by a radiologist via a graphical user interface (GUI). The training images may be stored with the manual delineation, for example, when a radiologist has previously examined the sequence as part of an earlier study (e.g., stored in the PACS and/or electronic medical record).

Optionally, one or more images without lesions are manually and/or automatically annotated to include normal tissue. Alternatively or additionally, tissue from a contralateral breast of a breast with a lesion is annotated.

At 308, each annotated lesion is associated with an indication. The indication may be stored, for example, as a label, a tag, metadata, a value of a field in an electronic medical record, according to the color of the delineation, and/or other representations. The indications are based on the desired classification categories of the trained deep CNN, for example, mass or no-mass, benign or malignant.

The images without lesions and/or annotated regions in the contralateral breast may be associated with an indication, for example, normal, or no-mass.

At, 310, each sequence is analyzed to identify the i-base image, the i-peak image, the i-early image, and the i-delay image, for example, as described herein with reference to act 106 of FIG. 1.

At 312, optionally, the patch distinctiveness saliency map is computed for one or more images of each sequence, for example, as described herein with reference to act 108 of FIG. 1.

At 314, optionally, the cross-saliency map is computed for one or more images of each sequence, for example, as described herein with reference to act 110 of FIG. 1.

At 316, the multi-channel image representation is created for each sequence, for example, as described herein with reference to act 114 of FIG. 1.

At 318, the deep CNN is trained, according to the multi-channel image representations, and the associated labels.

Optionally, the deep neural network is trained according to stochastic gradient descent. Optionally, the batch size is about 100 examples. Optionally, momentum is set to about 0.9. Optionally, the weight delay is set to about 0.0001. Optionally, the number of parameters of the deep CNN is set to less than about 140,000. Optionally, the training data is obtained from less than about 200 sample individuals. Optionally, the number of annotated lesions is less than about 200. Optionally, the number of labels images is less than about 2000.

At 320, the deep CNN is provided for classification of a target sequence of anatomical images, for example, stored as trained deep CNN 220A.

Various embodiments and aspects of the implementations of the systems, apparatus, methods, and/or code instructions as delineated hereinabove and as claimed in the claims section below find calculated support in the following examples.

EXAMPLES

Reference is now made to the following examples, which together with the above descriptions illustrate some embodiments of the systems, apparatus, methods, and/or code instructions described herein in a non limiting fashion.

In a first set of experiments, inventors performed a computational evaluation based on the three channel implementation of the multi-channel image fed into the neural network. The first set of experiments indicate the improved accuracy of classification of the neural network architecture described herein when fed the multi-channel image representation described herein, in comparison to a single channel image and/or an alternative classifier architecture. Moreover, the first set of experiments indicate the improved accuracy of classification of the neural network architecture described herein when trained with a reduced training dataset, in comparison to the alternative classifier architecture trained with the reduced training dataset.

The dataset included breast MRI studies from 123 female patients. Each study included Dynamic Contrast Enhanced (DCE) T1 sequences with one pre-contrast series and at least three post-contrast series. Three experienced breast radiologists interpreted the studies using only image information, without considering any clinical data. Each identified lesion was assigned a BI-RADS score, for example, as described with reference to "ACR BI-RADS® Atlas—American College of Radiology.", <www(dot)acr(dot)org/Quality-Safety/Resources/BIRADS> (15 Mar. 2016), as well as a descriptor of the lesion's margins and enhancement pattern. The boundaries of the lesion were manually delineated on each relevant slice, with an average of 8.8±6 annotated slices per patient. The lesion images were then cropped using a square bounding box around the annotated boundaries and scaled to the required input size of the neural network. For each lesion, an equal-size normal tissue bounding box was extracted from the contralateral breast. Overall, there were 173 annotated lesions, yielding 891 images (71%) labeled as malignant (BIRADS 5) and 365 images (29%) labeled as benign (BI-RADS 2).

The images were normalized to have zero mean and a unit standard deviation. The data set was augmented by adding three rotated (90°, 180°, 270°) and two flipped (left-right, up-down) variants, for each image.

The three channel implementation of the multi-channel image was computed according to the DCE T1 sequence(s), as described herein.

Figure 6:
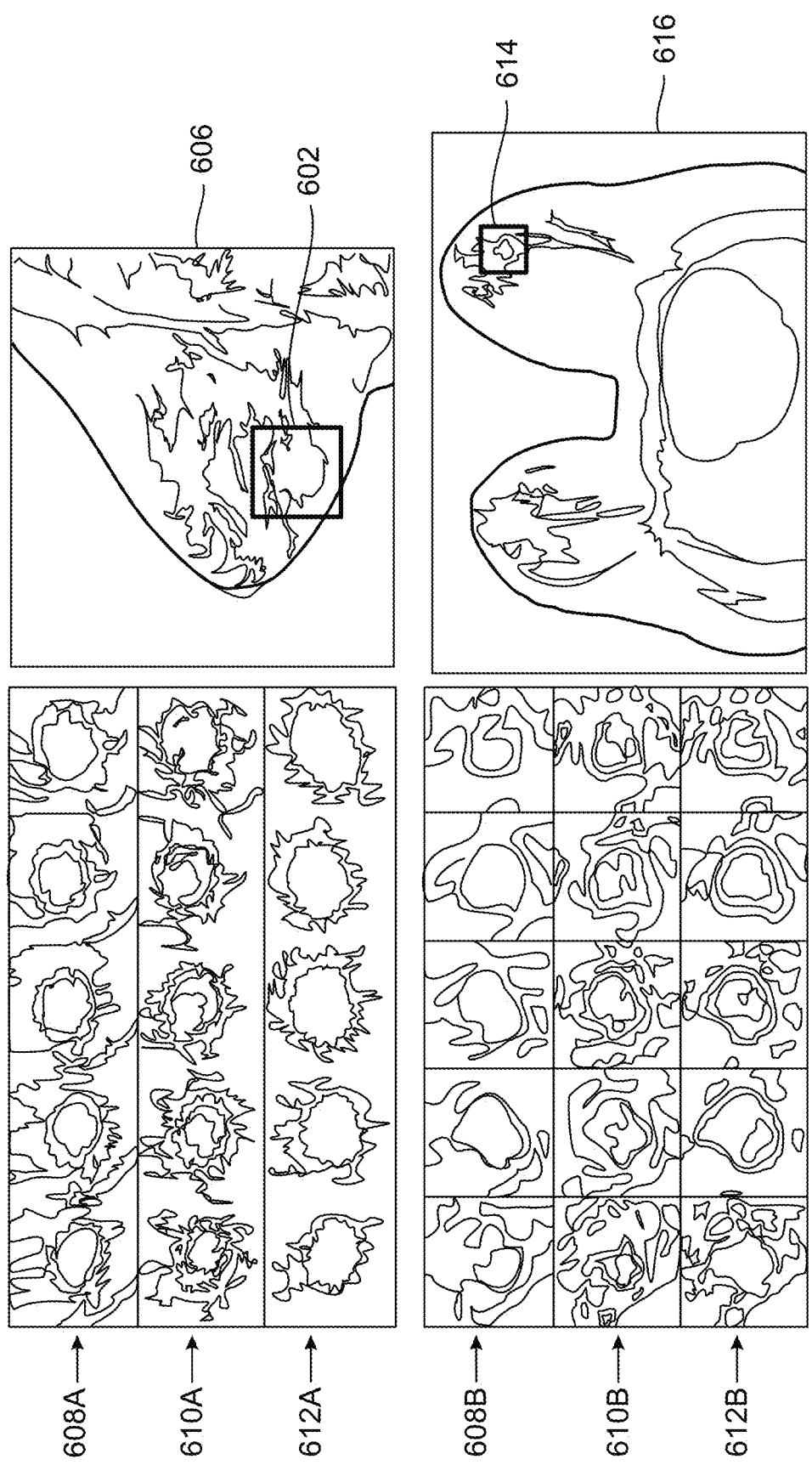
FIG. 6 includes images from each channel of the multi-channel image, as part of an experiment.

Reference is now made to FIG. 6, which includes images from each channel of the multi-channel image, computed from the DCE T1 sequence of the dataset of breast MRI studies, as part of an experiment. Boundary box 602 includes a malignant (invasive ductal carcinoma) lesion. Image 606 is cropped from multiple slices and represented by three image channels: 608A, 610A, and 612A. Boundary box 614 of image 616 includes a benign (fibroadenoma) lesion. Image 616 is associated with channels 608B, 610B, and 612B Channels 608A-B of respective images 606 and 616 denote T1 at peak contrast enhancement, channel 610A-B denote T1 subtracted image at peak enhancement, and channel 612A-B denote contrast washout. The images of channels 610A-B and 612A-B may be color coded to generate heatmaps, for example, as blue shades indicative of low values and red shades indicative of high values.

The network architecture used is based on the CIFAR-10 model, for example, as described with reference to Gubern-Merida et al. This network includes three consecutive blocks of convolution, pooling, and rectified linear unit (ReLU) layers, followed by a fully-connected layer and a softmax loss layer. The input image size was 32×32×3, and the number and size of the filters at the three convolution layers were 32×5×5×3, 32×5×5×32 and 64×5×5×32, respectively. The pooling layers operated on a 3×3 neighborhood with a stride of 2 pixels. The total number of network parameters was about 140K. The network was trained using stochastic gradient descent with a batch size of 100 examples, momentum of 0.9, and weight decay of 0.0001. The learning rate used was $5 \times 10^{-4}$ in the first 30 training epochs, then decreased to $10^{-4}$ and $5 \times 10^{-5}$ for an additional 10 epochs each.

The performance of the network architecture was compared to an alternative classifier architecture. The alternative classifier architecture includes a pre-trained network for feature extraction VGGNet, for example, as described with reference to Wu, S. et al., from the visual geometry group at the University of Oxford. The CNN-M architecture, for example, as described with reference to Chatfield, K., Simonyan, K., Vedaldi, A., Zisserman, A., "Return of the Devil in the Details: Delving Deep into Convolutional Nets," arXiv Prepr. arXiv . . . , 1-11 (2014) was selected. The alternative network includes an input layer size of 224×224×3, followed by five convolution layers, three fully connected layers, and a softmax layer with 1000 output nodes. The total number of parameters was about 138M (which is noted to be significantly higher than the CNN architecture). The network was pre-trained to classify 1000 object categories from ImageNet, with roughly 1.2M training images (which is noted to be significantly higher than the number of images used to train the neural network). Image features were extracted from the output of the fully connected layer f7, resulting in feature vectors of 1024D per image. These features were fed into a support vector machine (SVM) classifier with a linear kernel, to provide the output classification for each lesion.

Figure 7:
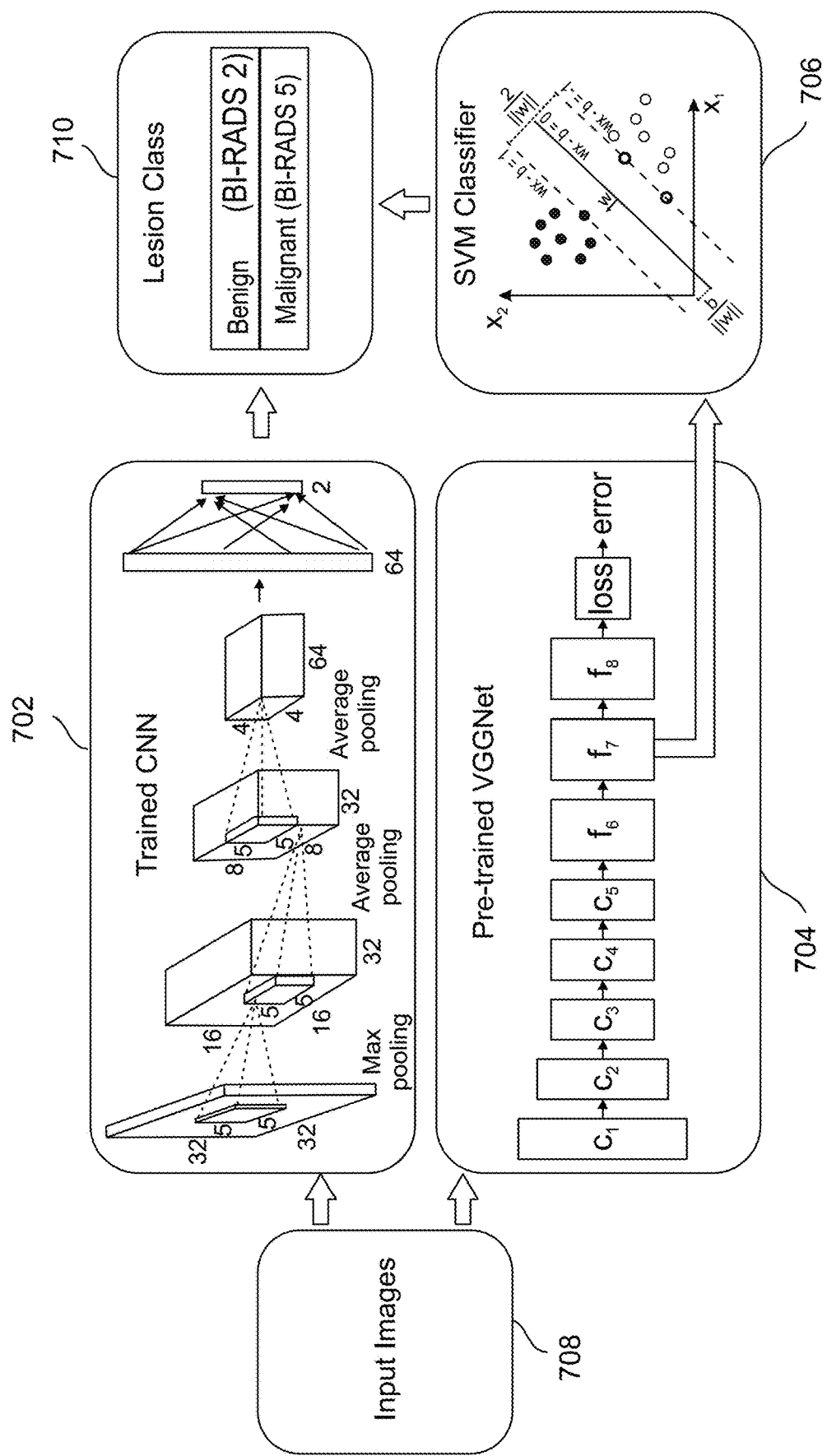
FIG. 7 is a schematic depicting the setup of the experiment described herein.

Reference is now made to FIG. 7, which is a schematic depicting the setup of the experiment described herein. The setup includes a trained CNN architecture 702 (that includes three convolution layers) and an alternative architecture (for comparison within the experiment) that includes a pre-trained VGGNet network 704 from which feature vectors are extracted from the fully connected layer (f7) and fed into a SVM classifier 706. The same input images 708 are fed as input into both architectures to generate classification results 710.

The two classifiers (CNN 702 and VGGNet 704+SVN classifier 706 as shown in FIG. 7) were compared in their ability to distinguish between benign and malignant lesions. Each classifier was first evaluated in a baseline configuration, which included three-channel image representation and data augmentation. Then, the number of image channels and the size of the training set were varied, and the effects on the classifiers' performance were examined In addition, the CNN classifier was evaluated on a three-class dataset, including benign, malignant, and normal images. All experiments used leave-one-patient-out cross-validation, in which for each tested patient, a model was trained using the images of all other patients. CNN training experiments were carried out using MatConvNet, for example, as described with reference to Vedaldi, A, Lenc, K., "MatConvNet," Proc. 23rd ACM Int. Conf. Multimed.—MM '15, 689-692, ACM Press, New York, N.Y., USA (2015) on a system with an Intel Core i7 CPU and a GeForce Titan-Black 6 GB GPU.

Execution of 50 training epochs on the dataset typically required 125 seconds to complete (2.5 seconds per epoch).

The baseline performance of both classifiers is summarized in Table 802 of FIG. 8. Table 802 includes classification results for the CNN classifier with one or three channel inputs compared with the SVM classifier using pre-trained VGG features (according to the architecture depicted in FIG. 7).

As shown in table 802, the designated CNN provided sensitivity and specificity of 0.84 and 0.82, respectively, which is more accurate than the pre-trained classifier, with area under the receiver operator characteristics curve (AUROC) of 0.91 versus 0.81 ($P<10$-6). Furthermore, the results presented in table 802 indicate that the three-channel image representation significantly contributed to the accuracy of the CNN classifier, compared to a single image channel (AUROC 0.91 vs. 0.85). It is noted that the pre-trained network demonstrated similar results when using either one channel or three channels. The CNN classifier was able to discriminate between three classes of benign lesions, malignant lesions, and normal tissue images with overall accuracy of 0.83, similar to the two class problem. In this configuration, the sensitivity and specificity of differentiating any lesion from normal tissue were 0.92 and 0.94, respectively.

Figure 9:
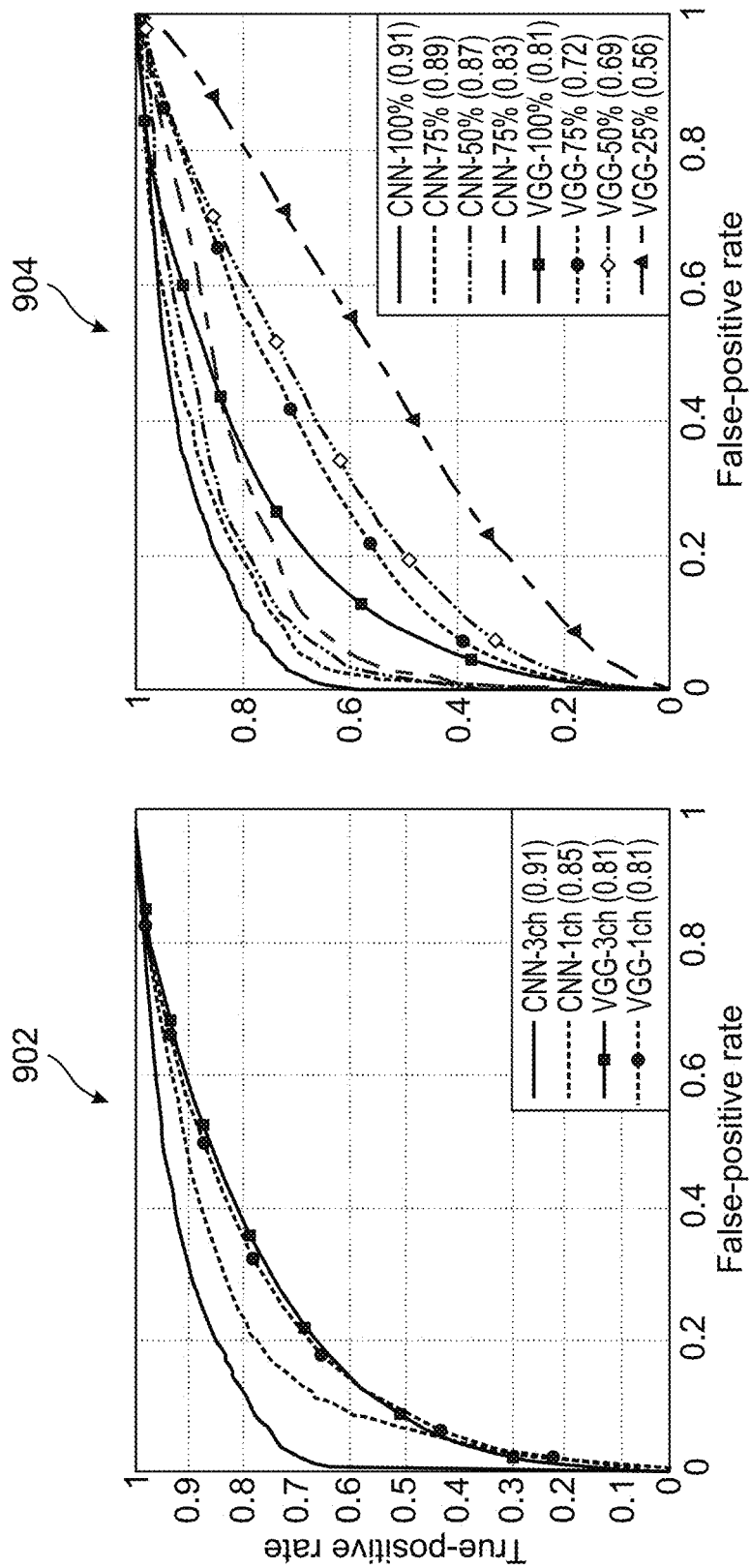
FIG. 9 includes a set of ROC curves indicative of results of the experiment described herein.

Reference is now made to FIG. 9, which includes a set of ROC curves for the CNN architecture 702 of FIG. 7, and another set of ROC curves for the SVM classifier 706 using pre-trained VGG features 704 of FIG. 7. ROC curves 902 and 904 represent three channel image representations and a single channel image. ROC curves 902 and 904 represent training with 100% of patient data, and reduced sets of patient data (75%, 50%, and 25% of the patients). Numbers in parenthesis are the area under the respective ROC curve.

Reference is now made to FIG. 10, which includes a table 1002 that summarizes the classification results of the CNN architecture in comparison to the SVM classifier using pre-trained VGG features, when trained with a reduced set of patients. The testing set included all 123 patients, using a leave-one-out cross-validation. The results indicative the improved accuracy of the CNN architecture when trained with reduced set of patient data in comparison to the alternative classifier architecture.

In a second set of experiments, inventors performed a computational evaluation based on the four and/or five channel implementation of the multi-channel image fed into the neural network.

A training dataset of 193 breast MRI studies from 171 female patients was used. The images were acquired through a variety of acquisition devices and protocols. Two publicly available resources Clark, K., Vendt, B., et al.: The Cancer Imaging Archive (TCIA): maintaining and operating a public information repository. J. Digit. Imaging. 26, 1045-1057 (2013) Lingle, W., Erickson, B. J., et al.: Radiology Data from The Cancer Genome Atlas Breast Invasive Carcinoma [TOGA-BRCA] collection. Bloch, B. N., Jain, A., Jaffe, C. C.: Data from breast-diagnosis, provided the data of 78 patients (46%). Each study included axial DCE T1 sequences with one pre-contrast series and at least 3 post-contrast series. Three breast radiologists interpreted the studies using image information alone, without considering any clinical data. Each identified lesion was assigned a BI-RADS score. The boundaries of the lesions were manually delineated on each relevant slice, with an average of 11±10 annotated slices per patient. Overall, there were 1957 annotated lesion contours in 1845 slices; 59% of them were labeled as malignant (BI-RADS 4/5) and 41% were labeled as benign (BI-RADS 2/3). The average lesion size was 319±594 $mm^2$. The patient data was partitioned into training (75%, 128 patients, 1326 slices) and testing (25%, 43 patients, 519 slices) subsets. The partitioning was random, while ensuring a similar distribution of benign and malignant lesions in each of the subsets.

The two-dimensional slice images were normalized to reduce data variability due to the mixture of studies from different sources. For each of the data subsets, the global 1% and 99% percentiles of pixel intensity were calculated for each channel, and contrast stretching was applied to convert all images to the same dynamic range. The breast area was segmented using U-Net, a fully convolutional network designed for medical image The five channel implementation of the multi-channel image representation described herein, was computed for the sequences of DCE T1 images segmentation, for example, as described with reference to Ronneberger, O., Fischer, P., Brox, T.: U-net: convolutional networks for biomedical image segmentation. In: Navab, N., Hornegger, J., Wells, W. M., Frangi, A. F. (eds.) MICCAI 2015. LNCS, vol. 9351, pp. 234-241. Springer, Cham (2015). The network was implemented using Lasagne, a python framework built on top of Theano. The neural network was trained on a subset of slices with manually delineated breast contours. The training process of 20 epochs on a batch size of 4 images required about 1 hour on a Titan X NVIDIA GPU. The region within the segmented breast underwent further processed.

Candidate regions detected for each slice (e.g., as described with reference to act 112 of FIG. 1) were cropped from their slice images using square bounding boxes. Window sizes were in the range of 5 to 50 pixels and normalized threshold values from 0.3 to 0.9. Bounding boxes were extended by 20% to ensure that the entire lesion was included in the cropped image. The extracted lesion images were resized to fit the CNN input, and 32×32×5 multi-channel images were created with 3 channels of the DCE image and 2 channels of the corresponding saliency maps.

The CNN architecture included of 9 convolutional layers in 3 consecutive blocks, for example, conceptually as described with reference to Hadad, O., Bakalo, R., Ben-Ar, R., Hashoul, S., Amit, G.: Classification of breast lesions using cross-modal deep learning. In: IEEE International Symposium on Biomedical Imaging (ISBI) (2017). The first block had two 5×5×32 filters with ReLU layers followed by a max pooling layer, the second block had four 5×5×32 filters with ReLU layers followed by an average pooling layer, and the final block had three convolutional layers of size 5×5×64, 6×6×64, and 3×3×64 respectively, each followed by a ReLU layer. The network was terminated by a fully connected layer with 128 neurons and a softmax loss layer.

The network output assigned either a mass or non-mass label to each bounding box. As the training data was unbalanced, with many more examples of non-mass regions, an ensemble of 10 networks was trained, each with a different random sample of non-mass regions. Majority voting of the ensemble determined the final classification.

For each slice, the output of the framework was a binary detection map, with regions that were proposed by the saliency analysis and classified as mass by the CNNs. The detection output per study was generated by summing the slice detection maps along the longitudinal axis. This produced a projected heatmap showing the spatial concentration of detected regions. Thresholding this heatmap was used to further reject false detections.

The ensemble of convolutional networks was trained on a set of 1564 bounding boxes of masses and 11,286 of non-masses, detected by the saliency analysis. The training set was augmented by adding three rotated and two flipped variants for each image. The networks were trained using MatCovNet, using a stochastic gradient descent solver with a momentum of 0.9. The average training time of 100 epochs was 20 min on NVIDIATitan-X black GPU. To evaluate the performance of the detection framework on the test set of 43 patients, all DCE slices of the test studies were processed. Overall, there were 5420 test slices, an average of 126 slices per patient. We compared the detection maps per slice and per study to the annotated ground-truth.

The unsupervised saliency analysis correctly detected 0.96 of true lesions in the entire dataset, with an average of 9.7 false positive detections per slice. The detection rates on the training and testing sets were similar. The average accuracy of mass/non-mass classification, obtained by the CNN on the validation set during the training process, was 0.86±0.02, with area under the receiver operator characteristics curve (AUC) of 0.94±0.01.

The evaluation of the entire detection framework on the test set slices yielded a sensitivity of 0.85 with 0.7 false-positives per slice. The CNN was able to reject 89% of the false candidate regions detected by the saliency analysis.

Reference is now made to FIG. 11, which includes tables 1102 and 1104 presenting results of the experiment. The results presented in table 1102 indicate that training with the 5-channel image representation achieved the highest accuracy. The results presented in table 1104 represent a comparison of the detection heatmaps per study with the projected ground-truth. The results indicate an improved sensitivity of 0.98 with an average of 7 false-positive detections per study.

Figure 12:
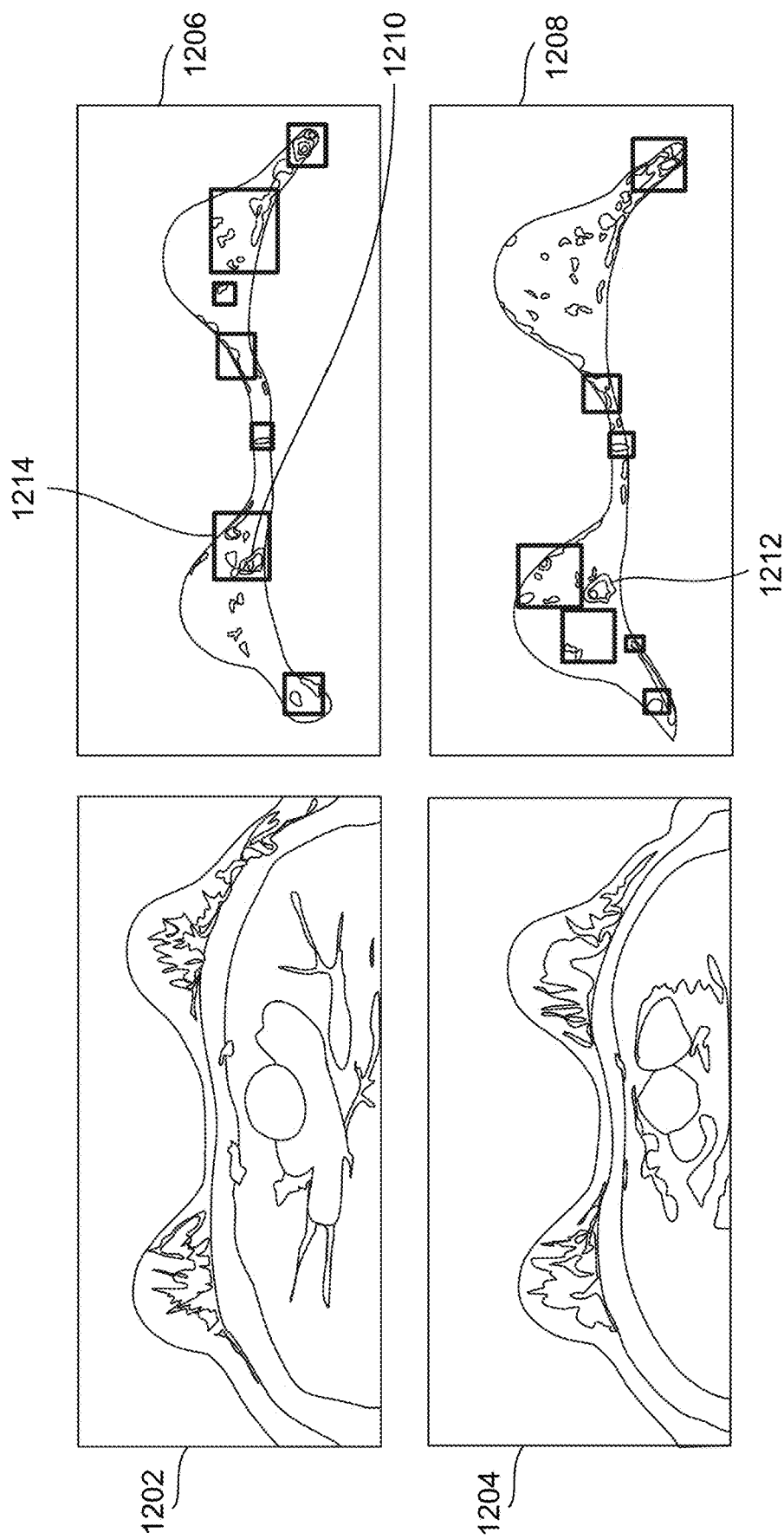
FIG. 12 includes images depicting examples of true-positive and false-negative detections, for illustrating the experiment described herein and/or in accordance with some embodiments of the present invention.

Reference is now made to FIG. 12, which includes images depicting examples of true-positive and false-negative detections, for illustrating the experiment and/or in accordance with some embodiments of the present invention. MRI images 1202 and 1204 include a BI-RADS 5 invasive ductal carcinoma in the right breast, shown in two peak-enhancement slices of the same sequence. Images 1206 and 1208 are corresponding cross-saliency maps. Regions 1210 and 1212 represent ground-truth contour. It is noted that for image 1206, the neural network correctly identified the region of the lesion (label 1214), while rejecting false detections (other box regions). As shown in 1208 (which is a consecutive slice of 1206), the same lesion at the consecutive slice was missed by the saliency analysis.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant sequences of anatomical images will be developed and the scope of the term sequence of anatomical images is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for detecting an indication of likelihood of malignancy for a sequence of anatomical images, comprising:
receiving a sequence of anatomical images of at least one portion of at least one breast of a target individual, wherein the sequence of anatomical images is acquired over a time interval during which contrast is administered to the target individual;
analyzing the sequence of anatomical images to identify the following images:
(i) a baseline pre-contrast image denoting lack of contrast within the sequence of anatomical images,
(ii) a peak contrast image denoting a peak contrast enhancement within the sequence of anatomical images,
(iii) an initial uptake image denoting initial contrast enhancement within the sequence of anatomical images,
(iv) a delayed response image denoting final contrast enhancement within the sequence of anatomical images;
creating a multi-channel image representation of the sequence of anatomical images comprising the following image channels:
(A) intensity channel including the peak contrast enhanced image,
(B) contrast-update channel including the computed difference between the peak contrast enhanced image and the pre-contrast image,
(C) contrast-washout channel including the computed difference between the initial uptake image and the delayed response image;
computing by a trained deep convolutional neural network (CNN), a classification category indicative of likelihood of malignancy for the sequence of anatomical images according to the multi-channel image representation and;
computing a patch distinctiveness saliency map by computing a statistical distance between each patch of a plurality of patches of at least one image of the sequence of anatomical images and an average patch along principal components of the plurality of patches;
wherein the multi-channel image representation further includes a patch distinctiveness saliency channel that includes the patch distinctiveness saliency map.

2. The method according to claim 1, wherein the sequence of anatomical images is extracted as two dimensional slices from three dimensional image data acquired by a Magnetic Resonance Imaging (MRI) machine executed a T1 weighted protocol of a dynamic contrast enhanced (DCE) study.

3. The method according to claim 1, wherein each one of a plurality of patch distinctiveness saliency maps is computed for a respective image of the sequence of anatomical images, and wherein the method further comprises creating a single patch distinctiveness saliency heat map by combining the plurality of patch distinctiveness saliency maps, wherein the patch distinctiveness saliency channel stores the single patch distinctiveness saliency heat map.

4. The method according to claim 1, further comprising analyzing the patch distinctiveness saliency map to identify candidate regions that include a relatively higher density of salient values compared to non-candidate regions.

5. The method according to claim 4, wherein the analyzing is performed by computing a score image according to a score assigned to each pixel according to salient values above a threshold within a region around the pixel, and applying non-maximal suppression to the score image to obtain a binary detection mask that includes the candidate regions indicative of the locations of local maxima.

6. The method according to claim 4, further cropping the candidate regions from the at least one image, and resizing each cropped candidate region according to the input of the deep CNN, wherein the deep CNN computes a classification category indicative of likelihood of malignancy for each of the candidate regions.

7. The method according to claim 6, wherein the deep CNN outputs a binary detection map that includes the candidate regions computed with the classification category indicative of likelihood of malignancy for each of the candidate regions.

8. The method according to claim 7, further comprising summing the values of the binary detection maps generated for each image of the sequence of anatomical images along a longitudinal axis, to generate a projected heatmap indicative of spatial concentration of candidate regions.

9. The method according to claim 1, further comprising:
computing a cross-saliency map that includes for each patch of a plurality of patches of one breast, the corresponding nearest neighbor patch in a contralateral breast, wherein the cross-saliency map stores cross-saliency values indicative of the distinctiveness of each patch of the plurality of patches;
the cross-saliency map is computed according to a statistical distance between each patch of a plurality of patches of one breast of at least one image of the sequence of anatomical images and corresponding patches of the contralateral breast of the at least one image,
wherein the multi-channel image representation further includes a cross-saliency channel that includes the cross-saliency map.

10. The method according to claim 9, wherein each one of a plurality of cross-saliency maps is computed for a respective image of the sequence of anatomical images, wherein the method further comprises creating a single cross-saliency heat map by combining the plurality of cross-saliency maps, wherein the cross-saliency channel stores the single cross-saliency heat map.

11. The method according to claim 9, wherein the cross-saliency map is computed by computing a contralateral patch flow according to a flow field between patches of left and right breasts for identifying for each patch of one breast the corresponding nearest neighbor patch in the contralateral breast, wherein a cross-saliency value of the cross-saliency map of each patch is estimated according to an error of the nearest neighbor patch.

12. The method according to claim 11, wherein the smooth motion field is assumed for computation of a dense flow field for each pixel by considering a patch around the respective pixel.

13. The method according to claim 12, wherein initially, for each pixel location, a random displacement vector is assigned, the random displacement vector marks a location of a corresponding patch in the contralateral breast, wherein a quality of the displacement vector is measured according to a computed distance between a certain patch of one breast and the corresponding patch of the contralateral breast, and further comprising attempting an improvement in displacement of a certain patch of the one breast according to displacement vectors of neighboring patches of the contralateral breast, and iterating between the assignment of the random displacement vector and improvement in displacement while storing the location of the best corresponding patch of the contralateral breast, according to the statistical distance.

14. The method according to claim 1, wherein the trained deep neural network includes nine convolutional layers in three consecutive blocks, the first block of the three consecutive blocks includes two 5×5×32 filters with Rectified Linear Unit (ReLU) layers followed by a max pooling layer, the second block of the three consecutive blocks includes four 5×5×32 filters with ReLU layers flowed by an average pooling layer, and the third block of the three consecutive blocks includes three convolutional layers of size 5×5×64, 6×6×64, and 3×3×64 each of the three convolutional layers followed by a ReLU, wherein the trained deep CNN is terminated by a fully connected layer with 128 neurons and a softmax loss layer.

15. A method for training a deep convolutional neural network (CNN) for detecting an indication of likelihood of malignancy for a sequence of anatomical images, comprising:
for each of a plurality of sample individuals:
receiving a respective sequence of anatomical images of at least one portion of at least one breast of a target individual, wherein the sequence of anatomical images are acquired over a time interval during which contrast is administered to the target individual, wherein a sub-set of images of the sequence of anatomical images include a manual delineation of boundaries of a lesion,
receiving an indication of the lesion as benign or malignant,
analyzing, the sequence of anatomical images to identify the following images:
(i) a pre-contrast image denoting lack of contrast within the sequence of anatomical images;
(ii) a peak contrast image denoting a peak contrast enhancement within the sequence of anatomical images;
(iii) an initial uptake image denoting initial contrast enhancement within the sequence of anatomical images;
(iv) a delayed response image denoting final contrast enhancement within the sequence of anatomical images;
creating a multi-channel image representation of the sequence of anatomical images comprising the following image channels:
(A) intensity channel including the peak contrast enhanced image;
(B) contrast-uptake channel including the computed difference between the peak contrast enhanced image and the pre-contrast image;
(C) contrast-washout channel including the computed difference between the initial uptake image and the delayed response image;
training a deep CNN to compute a likelihood of malignancy for a sequence of anatomical images of a target individual according to the multi-channel image representation of the plurality of sample individuals and;
computing a patch distinctiveness saliency map by computing a statistical distance between each patch of a plurality of patches of at least one image of the sequence of anatomical images and an average patch along principal components of the plurality of patches;
wherein the multi-channel image representation further includes a patch distinctiveness saliency channel that includes e patch distinctiveness saliency map.

16. The method according to claim 15, further comprising, for each of a plurality of sample individuals, extracting a normal tissue region from a contralateral breast of a certain image of the sequence of anatomical images, wherein the normal tissue region is associated with a label indicative of normal tissue.

17. The method according to claim 15, wherein the deep neural network is trained according to stochastic gradient descent, with a batch size of 100 examples, momentum of 0.9, and weight delay of 0.0001, wherein a number of parameters of the deep CNN is less than about 140,000, wherein a number of sample individuals is less than about 200, a number of annotated lesions is less than about 200, a number of labels image less than about 2000.

18. The method according to claim 15, further comprising:
computing a patch distinctiveness saliency map by computing a statistical distance between each patch of a plurality of patches of at least one image of the sequence of anatomical images and an average patch along principal components of the plurality of patches,
computing a cross-saliency map by computing a statistical distance between each patch of a plurality of patches of one breast of at least one image of the sequence of anatomical images and corresponding patches of the contralateral breast of the at least one image;
wherein the multi-channel image representation further includes a patch distinctiveness saliency channel that includes the patch distinctiveness saliency map and a cross-saliency channel that includes the cross-saliency map.

19. A system for detecting an indication of likelihood of malignancy for a sequence of anatomical images, comprising:
a non-transitory memory having stored thereon a code for execution by at least one hardware processor of a computing device, the code comprising:
code for receiving a sequence of anatomical images of at least one portion of at least one breast of a target individual, wherein the sequence of anatomical images are acquired over a time interval during which contrast is administered to the target individual;
code for analyzing the sequence of anatomical images to identify the following images:
(i) a baseline pre-contrast image denoting lack of contrast within the sequence of anatomical images,
(ii) a peak contrast image denoting a peak contrast enhancement of the sequence within anatomical images,
(iii) an initial uptake image denoting initial contrast enhancement within the sequence of anatomical images,
(iv) a delayed response image denoting the final contrast enhancement within the sequence of anatomical images;
code for creating a multi-channel image representation of the sequence of anatomical images comprising the following image channels:

(A) intensity channel including the peak contrast enhanced image,
(B) contrast-update channel including the computed difference between the peak contrast enhanced image and the pre-contrast image,
(C) contrast-washout channel including the computed difference between the initial uptake image and the delayed response image;
code for computing by a trained deep convolutional neural network (CNN), a classification category indicative of likelihood of malignancy for the sequence of anatomical images according to the multi-channel image representation and;
code for computing a patch distinctiveness saliency map by computing a statistical distance between each patch of a plurality of patches of at least one image of the sequence of anatomical images and an average patch along principal components of the plurality of patches;
wherein the multi-channel image representation further includes a patch distinctiveness saliency channel that includes the patch distinctiveness saliency map.

* * * * *